United States Patent
Lund et al.

(10) Patent No.: US 11,874,697 B2
(45) Date of Patent: Jan. 16, 2024

(54) SYSTEMS, MONITOR MOUNTS, MONITORS, RACKS, MODULES, AND CABLE HOLDERS

(71) Applicant: DRÄGERWERK AG & CO. KGAA, Lübeck (DE)

(72) Inventors: Peter A. Lund, Nashua, NH (US); Andrew T. Provencher, Lowell, MA (US); Zachary K. Hennings, Reading, MA (US); Rajesh S. Rane, Andover, MA (US); Thomas Swyst, Arlington, MA (US); Christopher Aiston, Mont Vernon, NH (US)

(73) Assignee: DRAGERWERK AG & CO. KGAA, Lübeck (DE)

( * ) Notice: Subject to any disclaimer, the term of this patent is extended or adjusted under 35 U.S.C. 154(b) by 116 days.

(21) Appl. No.: 17/526,771

(22) Filed: Nov. 15, 2021

(65) Prior Publication Data
US 2022/0075408 A1 Mar. 10, 2022

Related U.S. Application Data

(63) Continuation of application No. 16/883,507, filed on May 26, 2020, now Pat. No. 11,204,622.

(60) Provisional application No. 62/852,453, filed on May 24, 2019.

(51) Int. Cl.
*H05K 7/20* (2006.01)
*G06F 1/16* (2006.01)
*A61B 5/00* (2006.01)
*H01R 33/97* (2006.01)

(52) U.S. Cl.
CPC .......... *G06F 1/1607* (2013.01); *A61B 5/7445* (2013.01); *G06F 1/165* (2013.01); *G06F 1/1632* (2013.01); *G06F 1/1681* (2013.01); *H01R 33/97* (2013.01)

(58) Field of Classification Search
CPC .................................................... G06F 1/1632
See application file for complete search history.

(56) References Cited

U.S. PATENT DOCUMENTS

| 6,450,597 | B1* | 9/2002 | Bell | G06F 1/181 |
| | | | | 211/41.12 |
| 8,351,204 | B2* | 1/2013 | Yeo | H05K 7/1492 |
| | | | | 174/547 |
| 8,867,214 | B2* | 10/2014 | Ross | G06F 1/187 |
| | | | | 361/725 |
| 11,023,020 | B2* | 6/2021 | Wong | H05K 7/1427 |

(Continued)

*Primary Examiner* — Anthony Q Edwards
(74) *Attorney, Agent, or Firm* — Nolte Lackenbach Siegel

(57) ABSTRACT

A monitor mount is configured to detachably secure a monitor via a coupling which can be disengaged with an actuator. The monitor mount may be configured to detachably secure the monitor to a support structure via a clip. The monitor may have a reversible cover. The monitor may have a simplified back portion. The simplified back portion may omit couplings or electrical connections such that a back surface of the monitor is continuous. A rack is configured to detachably secure a module therein in multiple positions in which the module is mechanically connected to the rack and electrically connected or disconnected to the rack. The monitor may be a patient monitor and the module may be a patient monitoring module.

15 Claims, 30 Drawing Sheets

(56) References Cited

U.S. PATENT DOCUMENTS

2005/0146855 A1* 7/2005 Brehm ................. H05K 7/1454
361/788
2020/0371548 A1* 11/2020 Lund ..................... G06F 1/1632

* cited by examiner

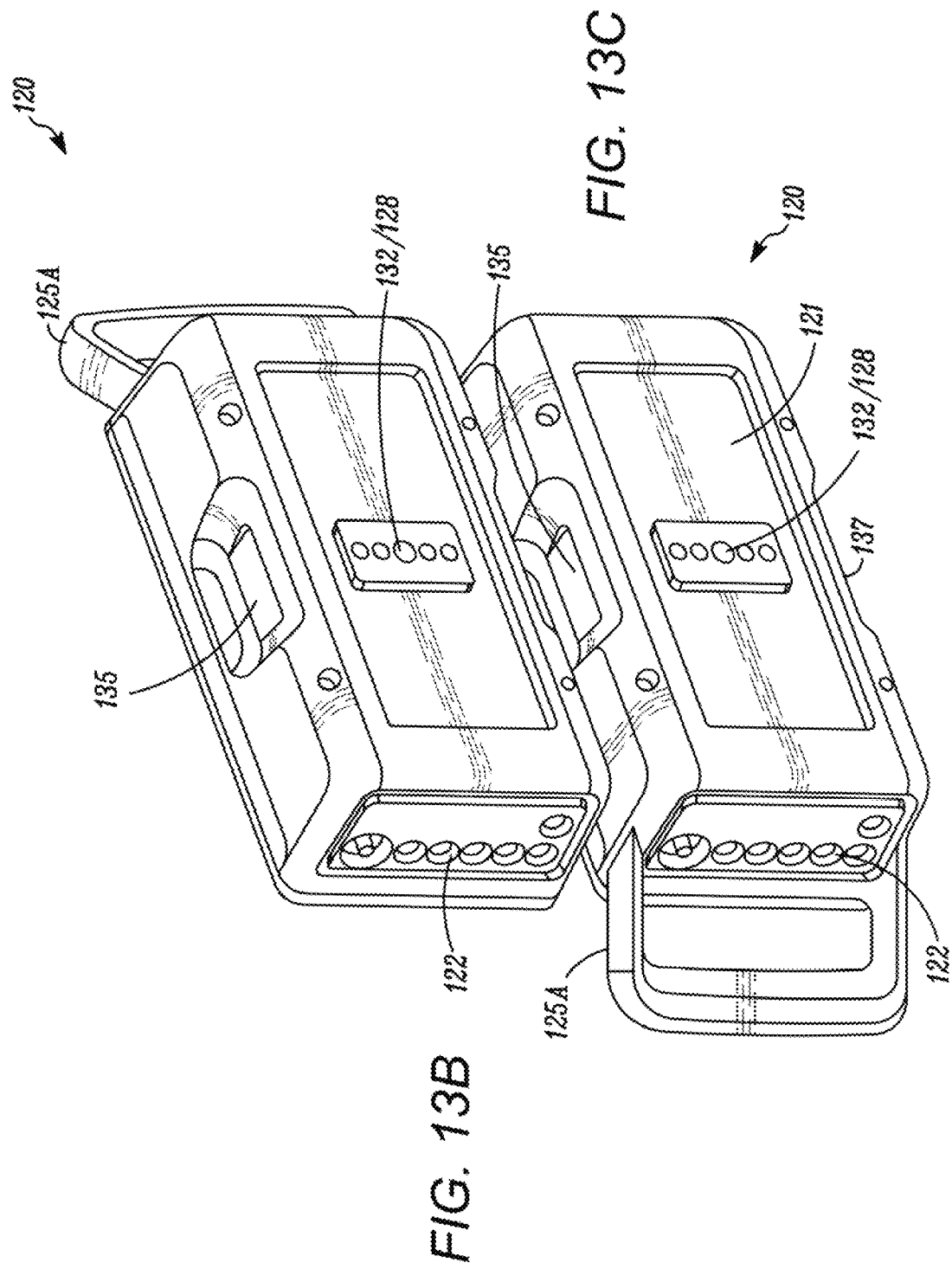

SYSTEMS, MONITOR MOUNTS, MONITORS, RACKS, MODULES, AND CABLE HOLDERS

CROSS-REFERENCE TO RELATED APPLICATIONS

This application is a continuation of co-pending U.S. patent application Ser. No. 16/883,507, filed May 26, 2020, claiming the benefit of provisional 62/852,453 filed May 24, 2019. The entire contents of the two applications are hereby incorporated by reference as though fully set forth herein.

FIELD OF THE DISCLOSURE

The present disclosure generally relates to: a monitor mount that is able to rigidly secure and quickly release differently sized monitors, and more specifically, to a monitor mount that enables data transfer between the monitor mount and a monitor received thereby; a monitor mount that is able to rigidly secure and quickly release a monitor to a support structure; a monitor with a reversible cover; a monitor with a simplified back portion; a rack that is able to secure a module in one of two different positions therein; and systems comprising any one or more of the above.

BACKGROUND OF THE DISCLOSURE

Monitors that include electronic visual displays are utilized in a large number of applications within a wide variety of industries including, for example, the healthcare industry, the military, and the oil and gas industry. Many of the applications within such industries require such monitors to, at times, be portable, and, at other times, be stationary. For example, in the healthcare industry, when not being used in transport of a patient or when a patient is ambulatory, monitors can be connected to a monitor mount. Such monitor mounts can provide a variety of functions including providing physical support, a power source, and a conduit to one or more computer networks.

One type of monitor is a patient monitor which is used by healthcare facilities to monitor and display information about a patient, such as vital signs, status of connected devices (e.g., physiological sensors, etc.), and the like. Patient monitors can be portable devices that travel with the patient in order to provide continuous monitoring during care. When a patient arrives at a hospital room or other treatment location, the patient monitor is often plugged into or otherwise connected to a patient monitor mount. Patient monitor mounts provide a physical interface for the patient monitor and are generally fixed to the treatment location. Patient monitor mounts can also provide electrical connection to other devices or infrastructure, such as power to recharge patient monitor batteries, network connectivity to other medical devices or hospital computer systems, and the like.

Patient monitors have different sizes and provide different functionalities. With current systems, each type of patient monitor typically requires a dedicated monitor mount, a dedicated controller, and a dedicated user interface. Accordingly, such monitors are not interoperable and the performance advantages of each type of monitor cannot be combined and leveraged.

In addition, there is a growing need in acute care environments to improve clinical workflow, reduce alarm fatigue, and customize medical devices to better suit hospital protocols and use models.

Due to the above problems associated with current systems, there is a need for a modular system providing a universal and scalable platform including a monitor mount capable of mixed use with monitors having different sizes which are interoperable with the same controller and the same user interface, and that can be quickly and universally docked to the monitor mount.

As discussed above, during the course of providing healthcare to patients, practitioners typically connect at least one type of sensor to a patient to sense, derive or otherwise monitor at least one type of patient medical parameter. Such patient connected sensors are further connected to a monitor that includes all relevant electronic components that enable conversion, manipulation and processing of the data sensed by the at least one type of sensor in order to generate patient medical parameters. These patient medical parameters may be stored in one or more modules and are usable by healthcare practitioners (e.g., nurses, doctors, physician assistants, or any other person charged with providing a healthcare service to a patient) in monitoring a patient and determining a course of healthcare to be provided to the patient. Additionally or alternatively, the one or more modules may contain data, such as patient treatment data, to be transferred to the monitor.

A monitor may be selectively connected to a patient at any point during which a healthcare professional comes into contact with the patient and may remain connected with the patient as the patient moves through various locations within a particular healthcare enterprise (e.g., hospital) or between different healthcare enterprises (e.g., an ambulance and/or different medical facilities). With conventional systems, the monitor and/or the module can be selectively connected (docked) to a stationary or fixed mount that may serve as a gateway for connecting the monitor and/or the module to a hospital information system (HIS) and/or a central monitoring station and allowing data representing the at least one patient medical parameter to be communicated to other systems within the healthcare enterprise. This data may then be used by different systems in further patient care.

It is difficult to both rigidly secure and quickly release monitors to conventional monitor mounts such that accidental release of a monitor is prevented. Conventional monitor mounts either do not prevent accidental release of a monitor or require time-consuming and burdensome removal of the monitor. In a hospital setting, rapid treatment and triage are often necessary. Therefore, a need exists to provide a monitor mount which enables both rigid securement of monitors thereto and quick release of monitors therefrom and also prevents accidental release of a monitor.

Conventional monitor mounts are also difficult to both rigidly secure to and quickly release from mobile or transportable support structures such as beds, stretchers, gurney rails, IV poles, ambulance bars, etc. in addition to stationary support structures. Conventional monitor mounts are not adapted to be attached directly to a support structure (e.g., a tubular or rectangular support structure), and generally must be mounted from the ceiling, on a wall, or on a cart. Furthermore, such mounting is time-consuming and burdensome in a hospital setting. Therefore, a need exists to provide a monitor mount that can be both quickly and rigidly secured to mobile or transportable support structures.

Conventional monitors typically have fixed covers that can only be secured in one orientation. This limits the versatility of the monitor and does not, for example, allow for left-hand and right-hand configurations with the same monitor. Therefore, a need exists to provide a monitor with a cover that is modular such that it can be reversibly secured in multiple different orientations.

Conventional monitors typically have complex back portions including electrical connections, physical connectors, and other types of interfaces such as optical interfaces. Such complex back portions can be difficult to grip, difficult to clean, and expensive to manufacture. Therefore, a need exists to provide a monitor with a simplified back portion.

Conventional racks for securing modules such as patient parameter modules are only capable of securing the modules in one position. That is, the modules are either fully secured in and electrically connected to the conventional racks or else the modules are electrically disconnected and completely released from the racks. When modules are not secured in the one position in the rack, they usually will fall or drop out of the rack due to gravity. The modules cannot be mechanically retained by the rack while being electrically disconnected from the housing. Also, a user must remove the modules and carry them to another location for transport or storage. However, there are a myriad of scenarios in which it is advantageous to store modules in a rack without an electrical connection therebetween. In this way, inactive modules do not consume power, do not require separate storage, and can be stored in the rack without further effort or possible misplacement. Therefore, a need exists to provide a rack which can store modules in an additional position in which the modules are physically connected to the rack but electrically disconnected from the rack.

Conventional cable holders are not adapted to secure many different types of cables. Moreover, conventional cable holders are not adapted to support and separate housing portions of cables. In addition, conventional cable holders generally cannot reduce cable clutter at the point of care, require complex mounting arrangements, and are not modular. In hospital settings where high acuity care is necessary, cable clutter and complex mounting arrangements are particularly time-consuming and burdensome. Therefore, a need exists to provide a cable holder that can provide at least one or more of the following: quick securement of many different types of cables, prevention of fraying or tangling of one or more cables, physical and/or electrical connectability to one or more devices such as patient monitoring devices, reduction of cable clutter at the point of care, and/or the ability to be readily cleaned and disinfected.

SUMMARY OF THE DISCLOSURE

In light of the above, the present disclosure is broadly directed to a system comprising a monitor mount, a first monitor and a second monitor. The monitor mount includes a first coupling, the first monitor includes a first electronic visual display and a first back portion, and the second monitor includes a second electronic visual display, a second back portion and a second coupling. The first monitor is configured to be detachably secured to the monitor mount by the first coupling. The second monitor is configured to be detachably secured to the monitor mount by the first coupling and an optional support portion. Each of the first back portion of the first monitor and the second back portion of the second monitor is configured to be detachably secured to the monitor mount by the first coupling. The first monitor is configured to be detachably secured to the second monitor by the second coupling. The second monitor is configured to surround at least a portion of the first electronic visual display of the first monitor when the first monitor is detachably secured to the second monitor. The second monitor can surround only a portion of the first monitor such that ends of the first monitor in a lateral direction of the first monitor are exposed. The monitor mount is able to secure each of the first monitor and the second monitor individually or both of the first monitor and the second monitor concurrently. In other words, the first coupling is configured to accept either the first monitor or the second monitor such that the monitor mount is configured to mount the first monitor alone, the second monitor alone, or a combination of the first monitor and the second monitor.

The monitor mount can also include a first power bus. The first monitor and/or the second monitor can optionally be powered by the first power bus when secured to the monitor mount.

The first monitor and/or the second monitor can also include a second power bus. If only one of the first monitor and the second monitor includes a second power bus, the other of the first monitor or the second monitor can be powered by the second power bus when the first monitor is secured to the second monitor. The first monitor and/or the second monitor, in some variations, is operable solely via the second power bus. In other variations, the first monitor and/or the second monitor is operable via either of the first power bus and the second power bus.

The first monitor and/or the second monitor can include a self-contained power source that allows the first monitor and/or the second monitor to be operated independently of the monitor mount.

The first monitor can include a sensor interface configured to receive data generated by at least one physiological sensor monitoring a physiological parameter of a patient. The at least one physiological sensor can include a wired connection to the sensor interface. The at least one physiological sensor can additionally or alternatively include a wireless connection to the sensor interface.

The second monitor can be a multiparameter monitor for continuously monitoring adult, pediatric and neonatal patients both at a bedside and on transport and can support all patient acuity levels hospital-wide.

Either of the first monitor or the second monitor can capture and display real-time vital signs at the bedside. Either of the first monitor or the second monitor can be used as a standalone monitor or in combination. The system of the present disclosure integrates patient data and provides continuous monitoring at the bedside and on transport.

The second monitor can be configured to be first coupled to the first coupling and/or the support portion and the first monitor can be configured to be subsequently coupled to the second coupling.

The first monitor can be configured to be coupled to and power the second monitor by the second power bus of the first monitor when neither of the first monitor and the second monitor are secured to the monitor mount.

The second monitor can be configured to be coupled to and power the first monitor by the second power bus of the second monitor when neither of the first monitor and the second monitor are secured to the monitor mount.

Each of the first coupling and the second coupling can take various forms including a mechanical coupling, an electro-mechanical coupling, and/or a magnetic coupling.

The monitor mount can further include a first communications interface coupled to at least one computing network. With this variation, the first monitor and/or the second monitor can include a second communications interface which transmits and receives data over the computing network via the first communications interface when the first monitor and/or the second monitor is secured to the monitor mount.

The monitor mount can also be configured to detachably secure one or more modules for monitoring the physiological parameter of the patient.

The monitor mount can be mounted at the bedside, from the ceiling, on a wall across the room, or even outside the room for isolation purposes.

The first monitor can visualize at least a portion of received data on the first electronic visual display. The second monitor can visualize at least a portion of received data on the second electronic visual display.

The first monitor can be configured to be detachably secured to and removed from a forward face of the monitor mount.

The first monitor can be configured to be transversely inserted into and removed from the second monitor. Furthermore, the first monitor can be configured to be transversely inserted into and removed from the second monitor from each of a first lateral direction of the second monitor and a second lateral direction of the second monitor, wherein the first lateral direction of the second monitor is opposite to the second lateral direction of the second monitor. Such transverse insertion and removal can be performed with one hand by the user. In other words, it is not necessary to perform two separate motions to transversely insert or remove the first monitor from the second monitor.

The system of the present disclosure enables pick and go transport of a patient from one care area of a hospital to another care area of the hospital without having to disconnect the patient from a patient monitor. For example, the system of the present disclosure streamlines workflows by being able to go from bedside to transport in the push of a button. Cables and modules can remain attached to the patient and parameters and alarms can continue to be monitored in real time, while recording data during travel. The system of the present disclosure can also provide seamless wired-to-wireless networking, so surveillance can be continuous. No disconnection or reconnection of leads is required and there are no gaps in monitoring or data acquisition. As a result, all parameters that are monitored at the bedside can continue to be monitored on transport.

The system of the present disclosure therefore allows monitors to be mixed and matched across different care areas and geographies such that workflow is optimized. The system of the present disclosure also requires fewer mounting points than current systems, thereby reducing installation and maintenance costs. Since the monitor mount and one or more monitors are integrated and consolidated, the space required for the system of the present disclosure is minimized. The system of the present disclosure can be used in dry and wet zones and contributes to an enhanced level of hygiene. According to caregiver preference, the system of the present disclosure can be scaled to the patient's needs—from basic monitoring to using the full range of all of the monitors. To support individual workflow, multiple monitors can be used, for example, to support anesthesiologists, perfusionists, and surgeons if a surgical display controller is used.

The system of the present disclosure provides a high acuity care system that improves aesthetics and ergonomics by allowing different caregivers to view the information they need at the same place. The system of the present disclosure can be used as part of a healthcare enterprise solution and can bring comprehensive information to the point of care, while continuously monitoring the patient. For example, the system of the present disclosure can provide access to images, lab results and other clinical data, while displaying real-time vital signs data at the point of care. Furthermore, the performance advantages of differently sized monitors can be combined and leveraged. For example, the portability of a smaller monitor and the increased functionality of a larger monitor can be independently or concurrently capitalized upon.

The subject matter described herein provides many technical advantages. For example, the current subject matter enables the mounting of two monitors having different sizes, shapes, and functionality on a single monitor mount.

The monitor mount of the present disclosure can be both quickly and rigidly secured to mobile or transportable support structures in addition to stationary support structures. The monitor mount of the present disclosure therefore addresses deficiencies of difficulty in both quickly and rigidly securing devices to mobile or transportable support structures such as bed or stretcher or gurney rails, IV poles, ambulance bars, etc. in addition to stationary support structures, and failing to enable a monitor to be attached directly to a tubular or rectangular support structure.

The first monitor of the present disclosure may have a cover that is modular such that it can be reversibly secured in multiple different orientations. The first monitor therefore allows for left-hand and right-hand configurations with the same monitor.

The second monitor of the present disclosure may have a simplified back portion. Accordingly, the simplified back portion may have a reduced thickness and the second monitor may have a slimmer overall volume.

The rack of the present disclosure can store modules in an additional position in which the modules are physically connected to the rack but electrically disconnected from the rack. The rack of the present disclosure therefore addresses deficiencies of only being able to secure modules in one position inside a rack, and electrically disconnected modules falling or dropping out of the rack due to gravity.

The cable holders of the present disclosure can provide flexibility in mounting and cable management by being able to be quickly secured to and released from mobile or transportable support structures such as bed rails, stretcher rails, gurney rails, IV poles, ambulance bars, GCX rails, carts, etc., in addition to stationary support structures such as workstations, ceilings, or walls; and prevent fraying or tangling of one or more cables configured to physically and electrically connect to one or more devices such as patient monitoring devices. The support structure can be, for example, tubular or rectangular. Furthermore, the cable holders can manage a plurality of cables.

The cable holders can be standardized and can consolidate a plurality of cables such as shielded cables and ribbon cables. The cable holders can protect the cables from potential sources of contamination. The cable holders therefore optimize the workplace by reducing cleaning and disinfection time, improving workplace organization, reducing the risk of equipment being accidentally disconnected, optimizing workflow through well-structured workplace design, and reducing the risk of contamination. In other words, the cable holders can keep lines and cables out of the way and free of dust and other potential contaminants so as to help maintain a clutter-free workspace and prevent microbial contamination of equipment and patients. For example, nosocomial infections are a significant source of morbidity and mortality.

Tangled cables can cause a great deal of frustration, lost time, and patient discomfort. Managing the clutter that results from conventional cables is a tedious, time-consuming distraction that takes focus away from patient care. As cables are attached, they must be untangled and properly routed. The cable holders enable caregivers to spend more time with patients and less time sorting out cables. The cable holders eliminate the tangled clutter and hazards, in the operation room and intensive care unit, for example, that frequently occur with traditional cables and reduces visual overload for patients. The cable holders are durable, fast and easy to apply to a support structure, and are easy to clean because they wipe clean with standard disinfectants.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The following detailed description references the drawings, wherein:

FIG. 13B is a rear perspective view of the exemplary implementation of the first monitor 120 with a cover 125 thereof in a first orientation.

FIG. 13C is a rear perspective view of the exemplary implementation of the first monitor 120 with the cover 125 thereof in a second orientation.

DETAILED DESCRIPTION

Figure 1:
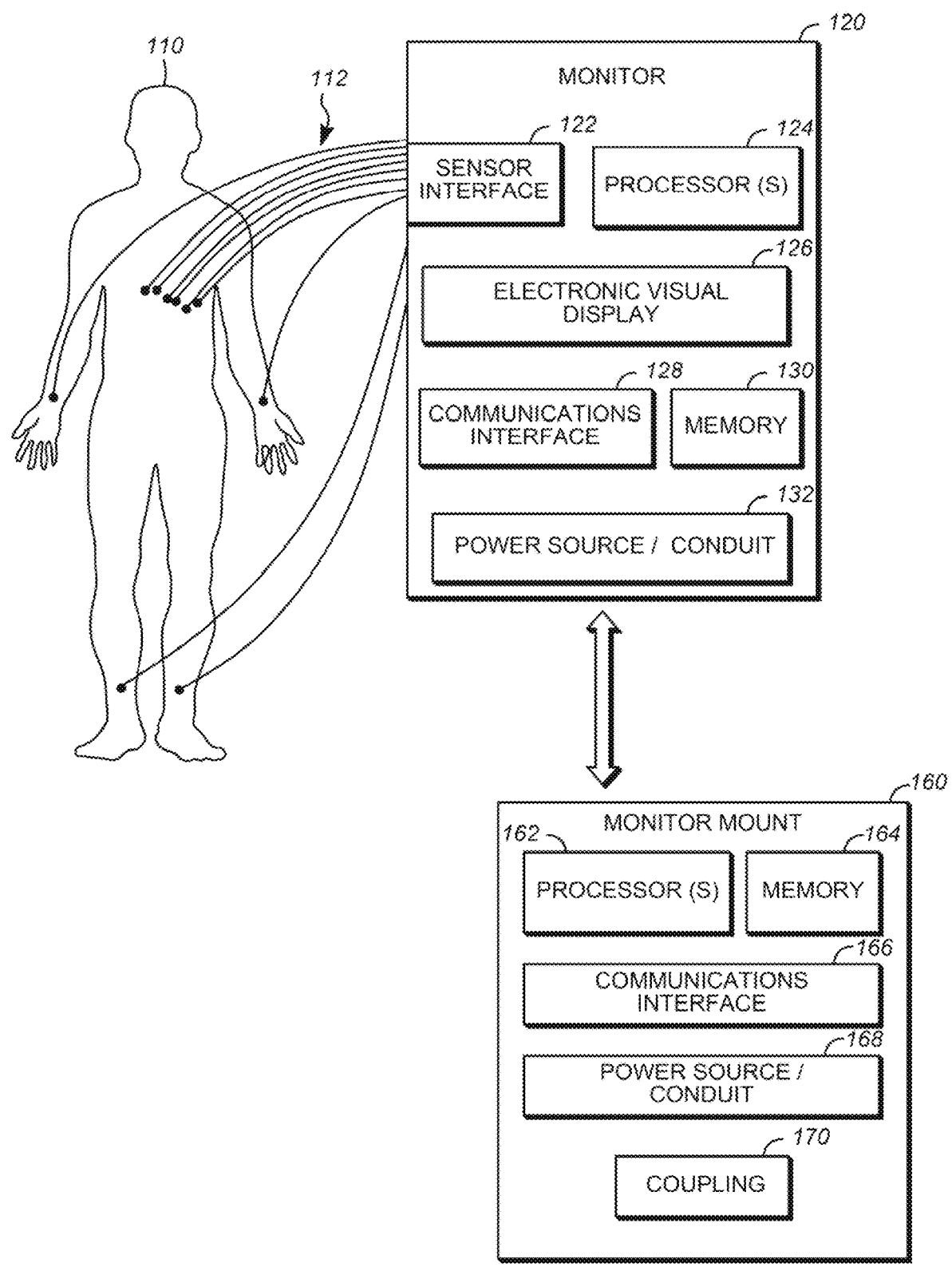
FIG. 1 is a logical diagram illustrating an example system including a monitor 120, and a monitor mount 160.

The following description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

The terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

It is to be understood that the singular forms "a", "an", and "the", include plural referents unless the context clearly dictates otherwise. Thus, for example, reference to "a processor" or "a memory" includes reference to one or more of such processors or memories.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted.

The subject matter described herein is directed to systems and apparatuses directed to monitors (e.g., display monitors having visual electronic displays) and monitor mounts providing physical support and, in some cases, power and access to a communications/computer network. Use of such systems and apparatuses can, for example, occur in a medical environment such as the scene of a medical event, an ambulance, a hospital or a doctor's office. When a patient undergoes initial patient monitoring in such an environment, a minimum set of sensors can be connected to a patient to collect various types of patient information as described in detail herein. As a patient is moved from one area of care within the medical environment to another area of care, the patient monitor can travel with the patient. In some situations, the patient monitor can be mounted to a monitor mount to provide for stationary observation of the patient information on a visual electronic display. During the course of patient monitoring, the number of sensors can also increase due to increased testing and/or monitoring of the patient. In such a scenario, a patient monitor initially monitoring the patient can be docked into monitor mount having a second, larger monitor in order to expand the number of sensors available for patient monitoring and/or increase the number of patient parameters on a single visual electronic display by docking the smaller patient monitor within a larger patient monitor. The initial patient monitor can either remain within the larger patient monitor or be removed from the larger patient monitor.

An example system may include at least one of a first monitor 120, a second monitor 140, a first exemplary implementation of a monitor mount 160, a second exemplary implementation of a monitor mount 160, a rack 200, a module 300, a cable holder 400 or 500, and a cable 600.

FIG. 1 is a logical diagram illustrating the example system including a monitor 120, and a monitor mount 160.

Figure 2:
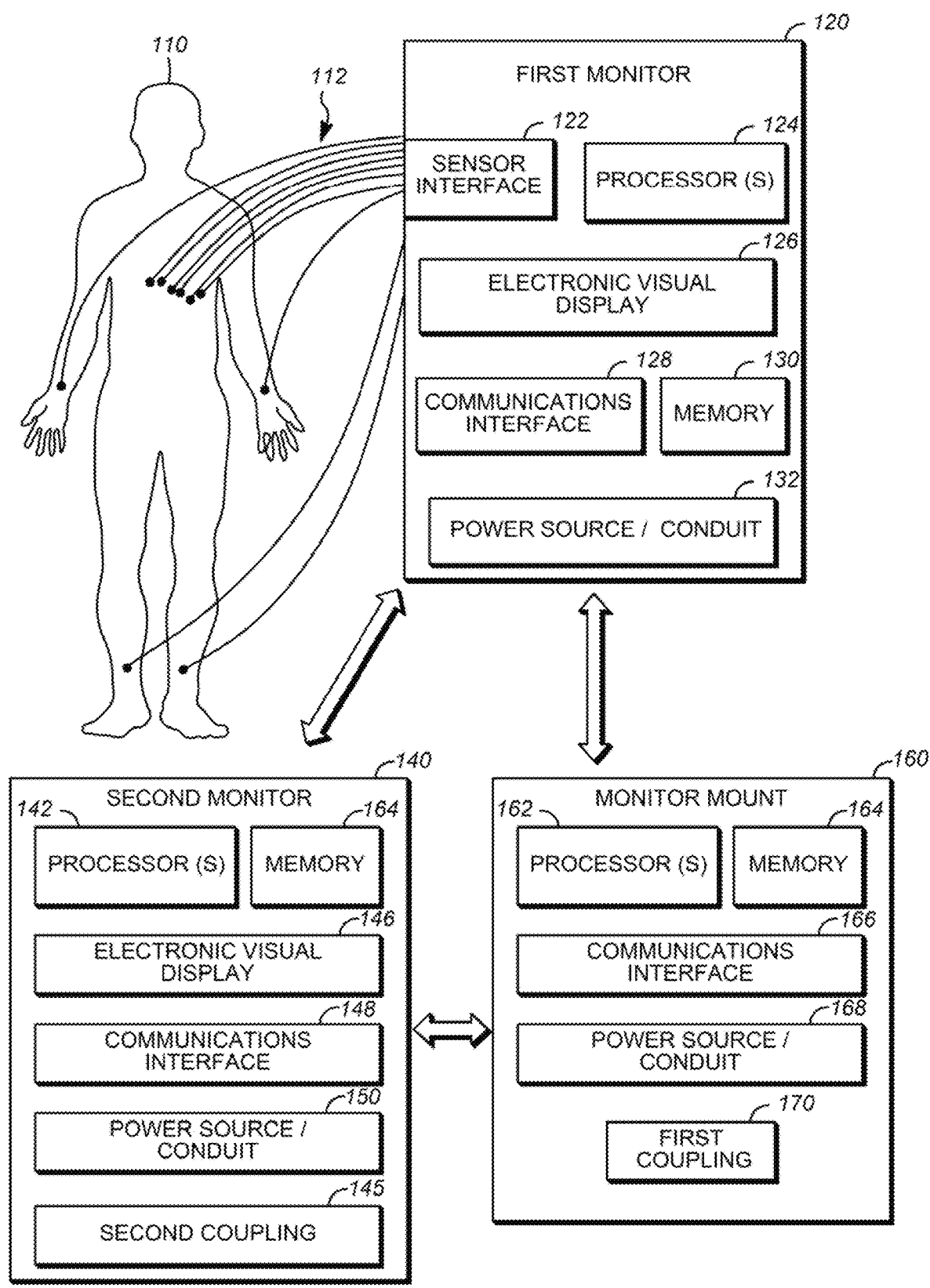
FIG. 2 is a logical diagram illustrating an example system including a first monitor 120, a second monitor 140, and a monitor mount 160.

FIG. 2 is a logical diagram illustrating the example system including a first monitor 120, a second monitor 140, and a monitor mount 160.

Figure 3:
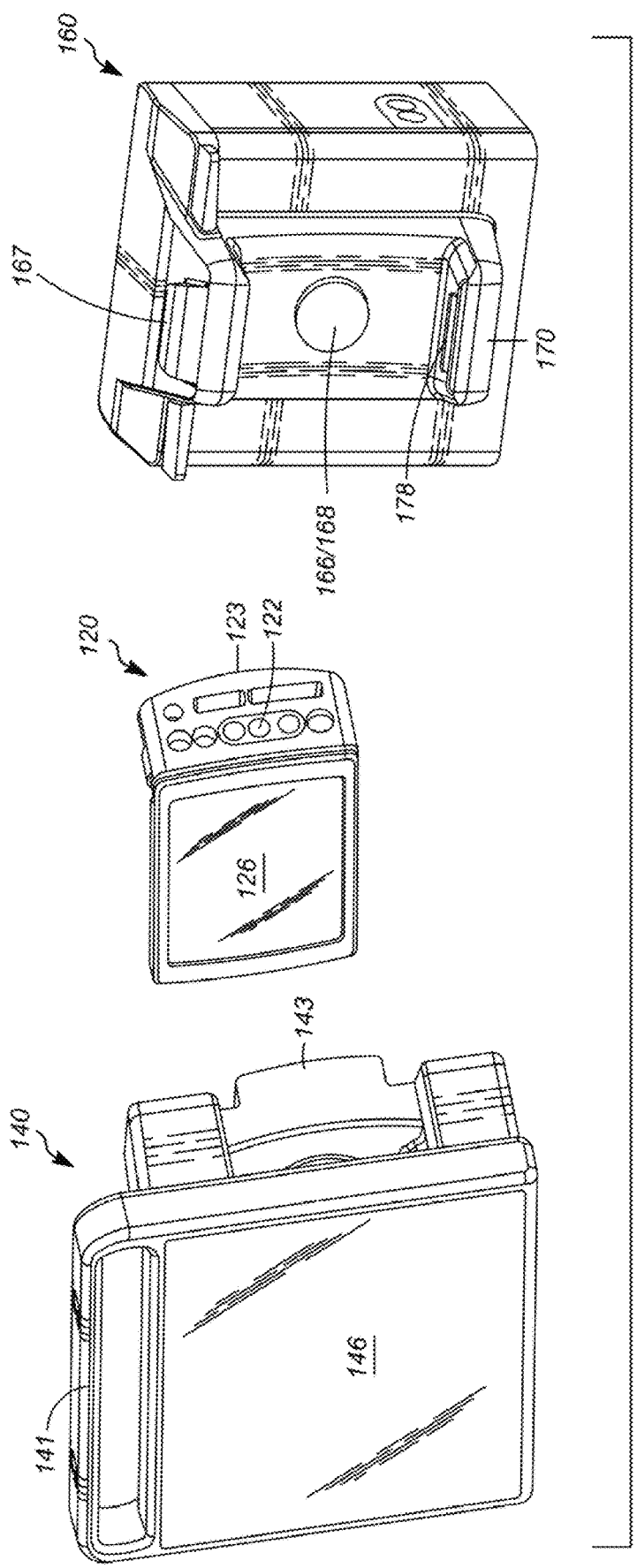
FIG. 3 is an exploded perspective view of the example system including the first monitor 120, a first exemplary implementation of the second monitor 140, and a first exemplary implementation of the monitor mount 160.

In the embodiment shown in FIG. 3, the monitor mount 160 can detachably secure (or otherwise physically interface with) the first monitor 120 and/or the second monitor 140.

In FIGS. 4-11, various exemplary embodiments of the monitor mount 160 are shown.

Figure 12:
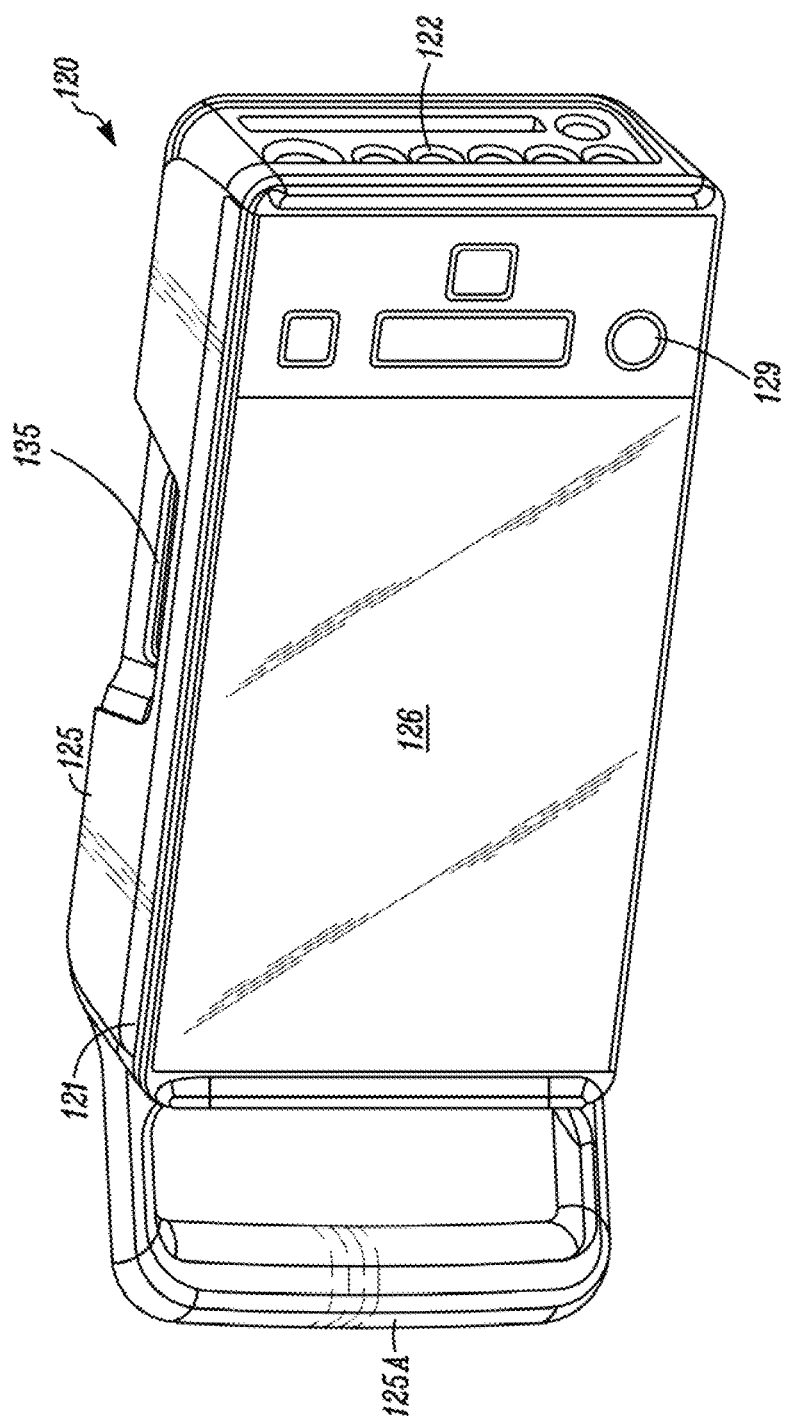
FIG. 12 is a front perspective view of an exemplary implementation of the first monitor 120.

In FIGS. 12-13C, an exemplary embodiment of a first monitor 120 is shown.

In FIGS. 14-19, various exemplary embodiments of a second monitor 140 are shown.

Figure 20:
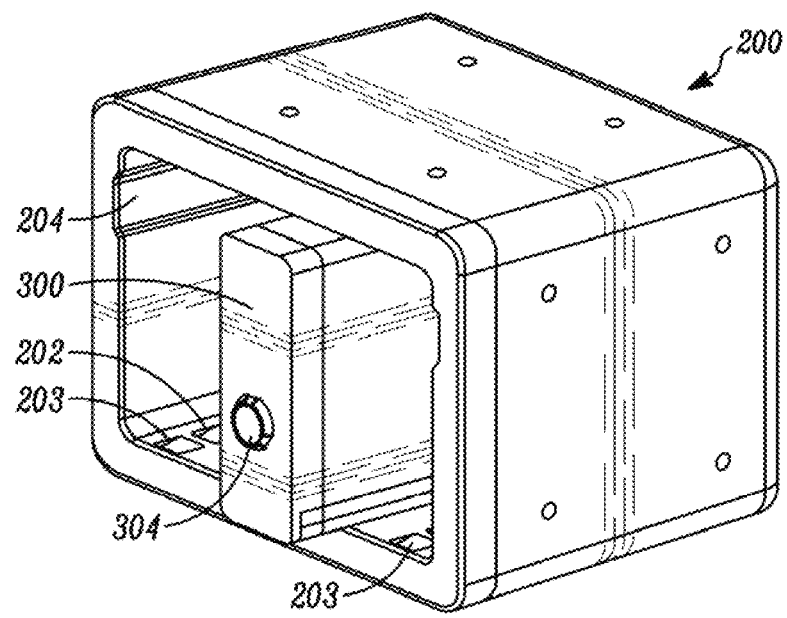
FIG. 20 is a front perspective view of an exemplary implementation of a rack 200 detachably securing an exemplary implementation of a module 300.

In the embodiment shown in FIG. 20, the rack 200 can detachably secure (or otherwise physically interface with) one or more modules 300.

Figure 21:
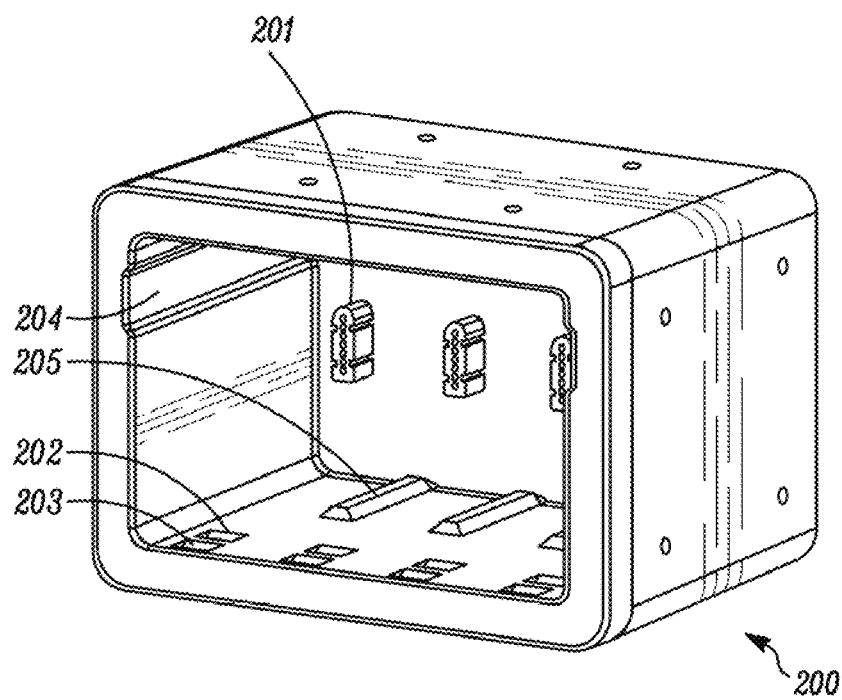
FIG. 21 is a front perspective view of the exemplary implementation of the rack 200.

In FIG. 21, an exemplary embodiment of a rack 200 is shown.

Figure 22A:
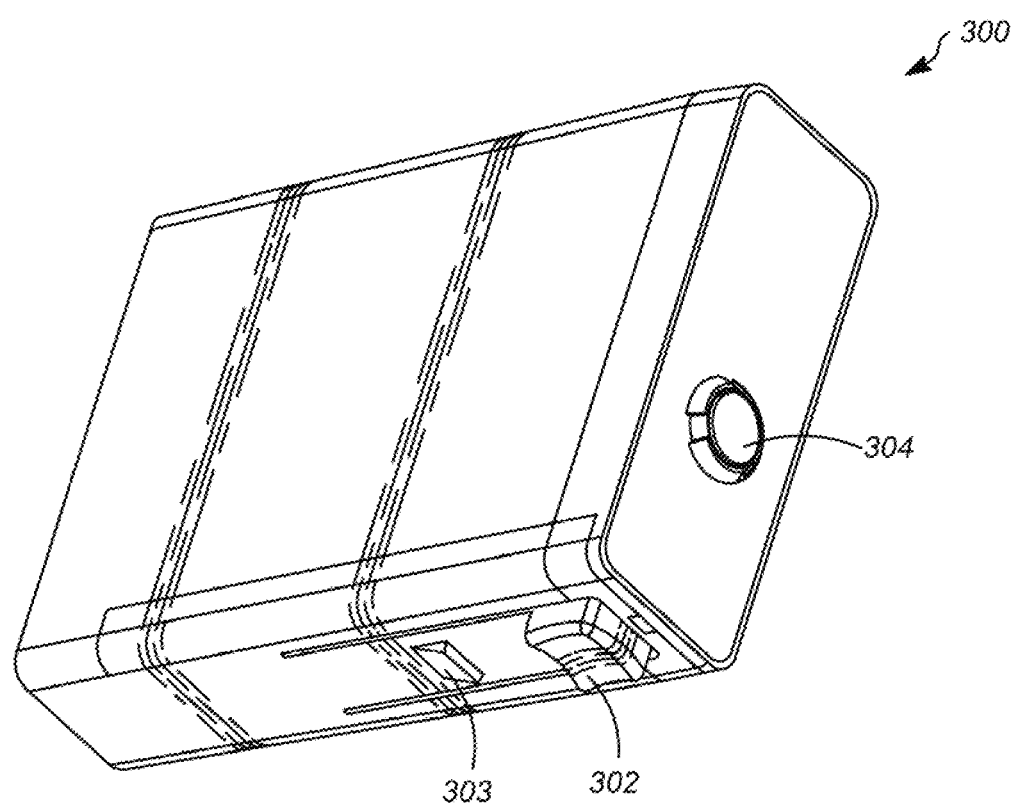
FIG. 22A is a bottom perspective view of an exemplary implementation of the module 300.

In FIG. 22A, an exemplary embodiment of a module 300 is shown.

In the embodiments shown in FIGS. 22B-24, the rack 200 can detachably secure (or otherwise physically interface with) one or more modules 300.

In the embodiments shown in FIGS. 22B-24, the rack 200 can detachably secure (or otherwise physically interface with) one or more modules 300.

Figure 25:
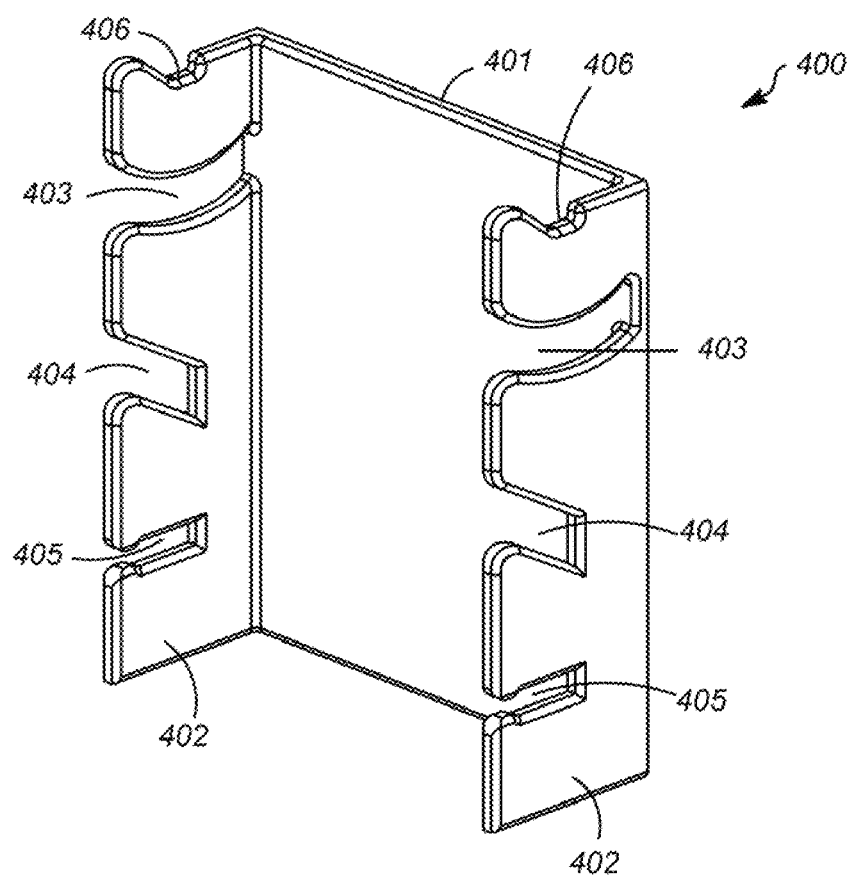
FIG. 25 is a front perspective view of an exemplary implementation of a cable holder 400.

In FIG. 25, an exemplary embodiment of a cable holder 400 is shown.

Figure 26:
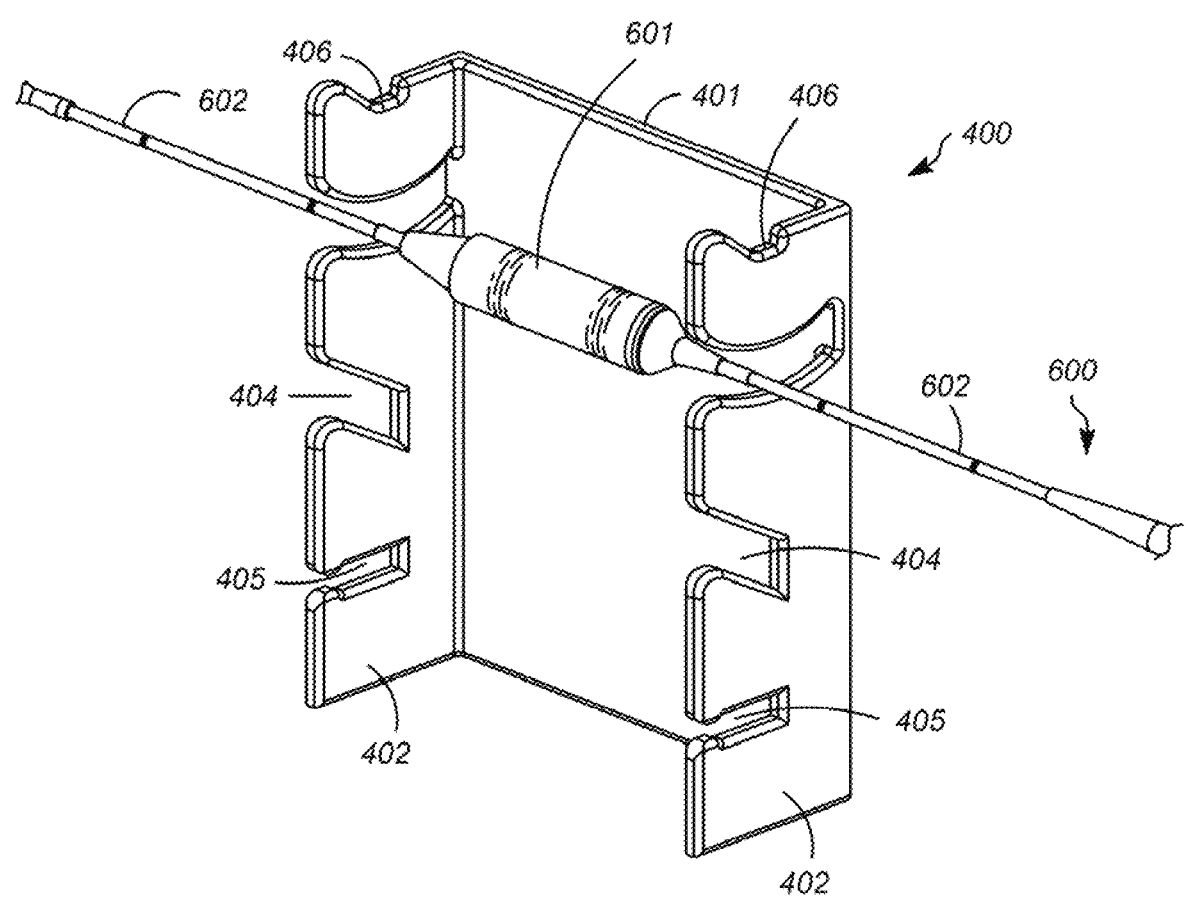
FIG. 26 is a front perspective view of the exemplary implementation of the cable holder 400 detachably securing a cable 600.

In the embodiment shown in FIG. 26, the cable holder 400 can detachably secure one or more cables 600.

Figure 27:
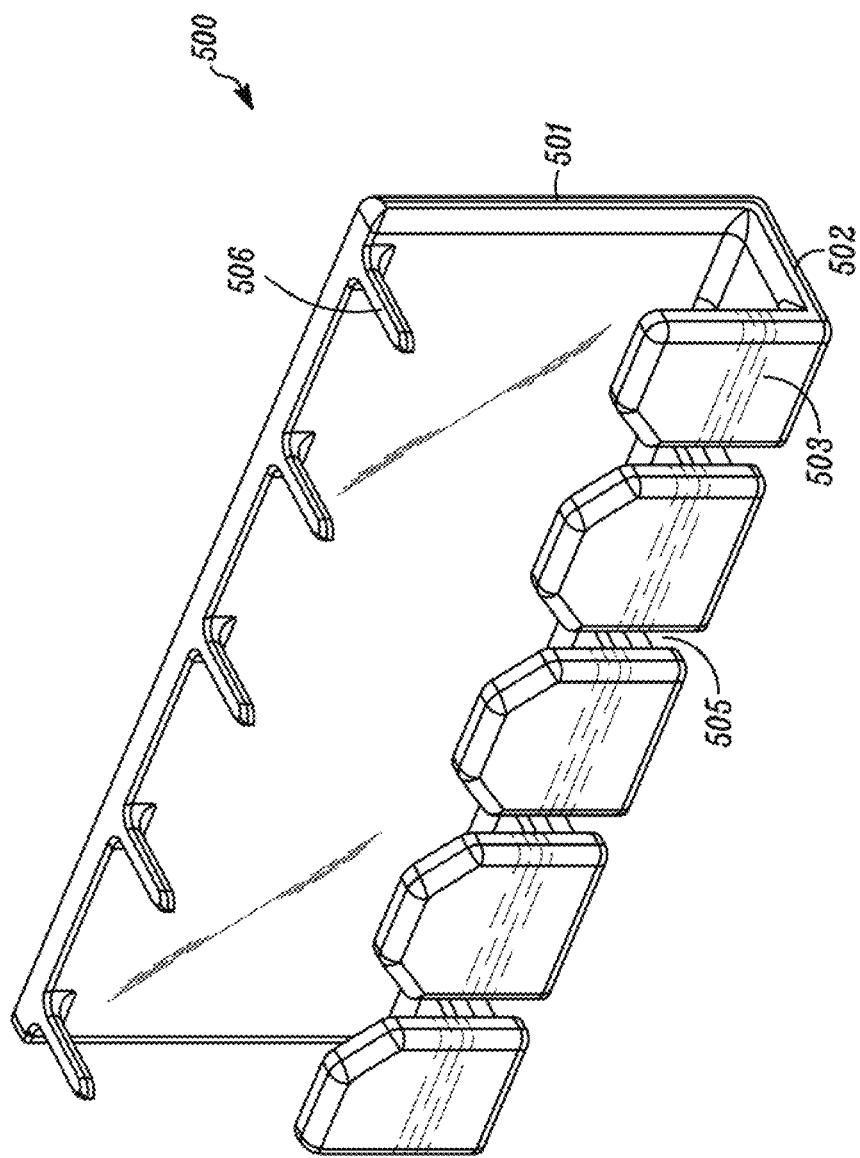
FIG. 27 is a front perspective view of an exemplary implementation of a cable holder 500.
Figure 28:
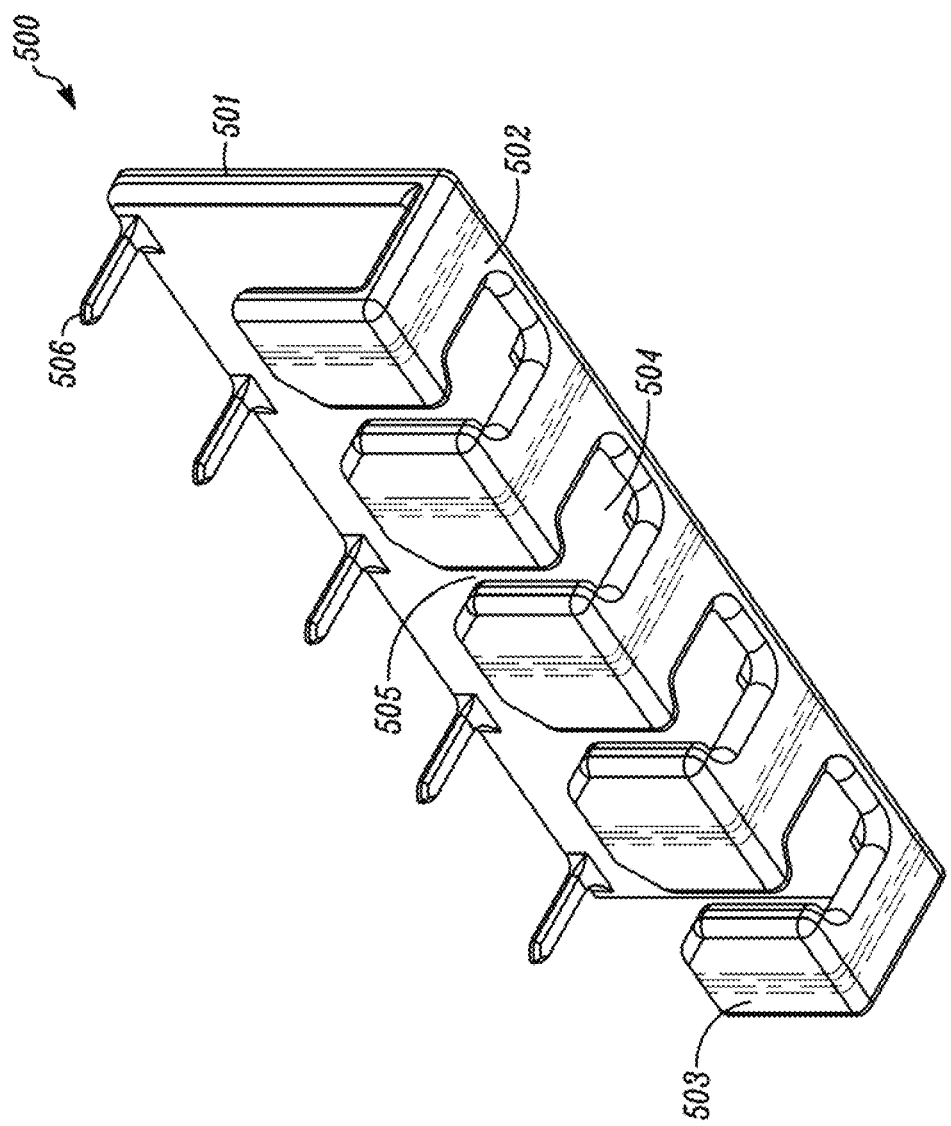
FIG. 28 is a bottom perspective view of the exemplary implementation of the cable holder 500.

In FIGS. 27 & 28, an exemplary embodiment of a cable holder 500 is shown.

Figure 29:
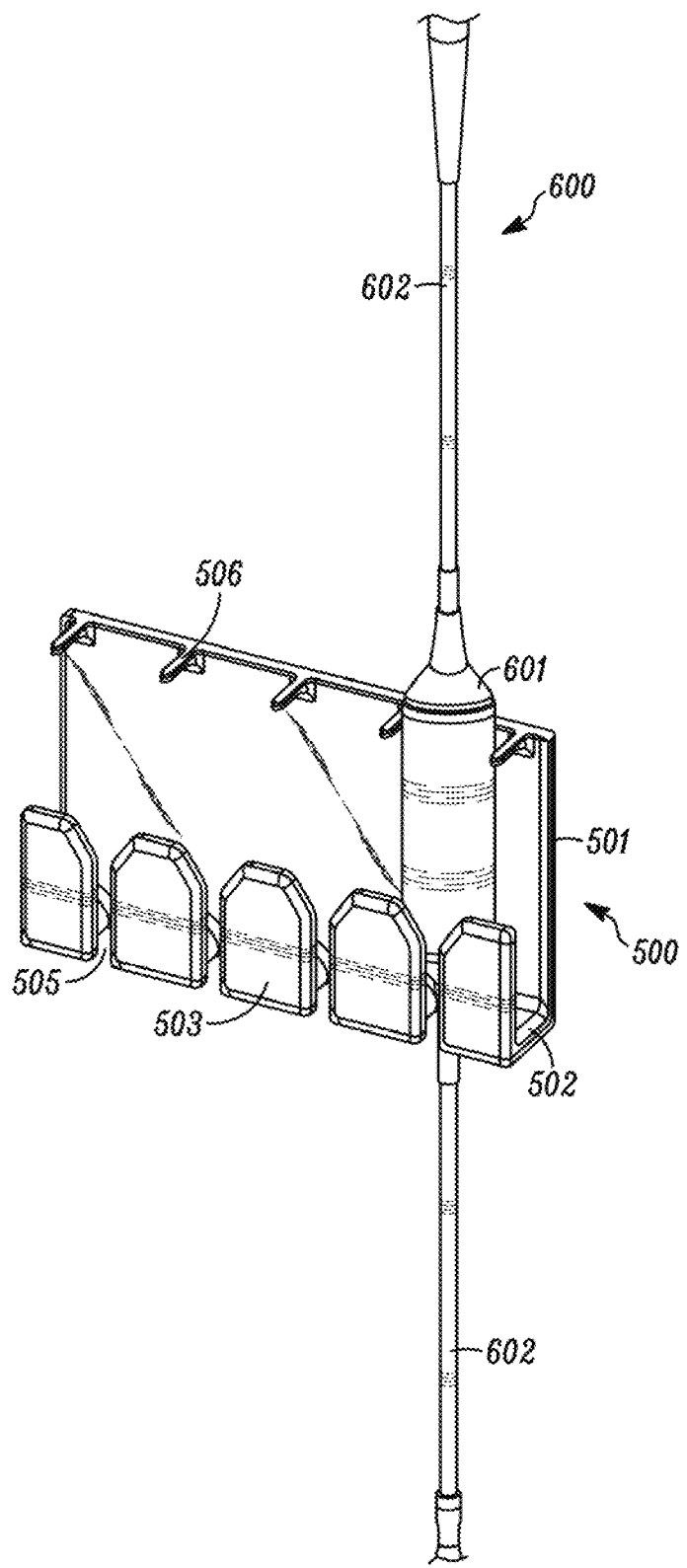
FIG. 29 is a front perspective view of the exemplary implementation of the cable holder 500 detachably securing a cable 600.

In the embodiment shown in FIG. 29, the cable holder 500 can detachably secure one or more cables 600.

In an exemplary implementation, a first exemplary implementation of the monitor mount 160 may be detachably secured to a support structure (e.g., a wall-mounted arm) (not shown) via an attachment mechanism such as a Video Electronics Standards Association (VESA) mounting interface adapted to an attachment mechanism in a hospital room in which a patient is being monitored and/or treated via one or more modules 300, for example, one or more physiological sensors and/or medical devices. The monitor mount 160 may detachably secure the second monitor 140, and the second monitor 140 can detachably secure (or otherwise physically interface with) the first monitor 120. The rack 200 may be coupled to the monitor mount 160 via a coupling. The rack 200 may detachably secure one or more of the modules 300. In lieu of or in addition to the first exemplary implementation of the monitor mount 160, a second exemplary implementation of the monitor mount 160 may be detachably secured to a support structure (e.g., a bed rail) (not shown) to await use on transport for detachably securing the first monitor 120, for example. Alternatively, the second exemplary implementation of the monitor mount 160 may serve as a stationary monitor mount.

Therefore, the example system provides an interconnected, versatile, and comprehensive patient care solution with a high degree of configurability. The example system acquires data at the bedside and on transport, without having to disconnect a patient as he or she is moved from care area to care area. The example system can be scaled depending on the patient's changing acuity level and medical devices can be customized to better suit hospital protocols and use models. Accordingly, the example system thereby improves clinical workflow.

The module 300 can provide one or more different functions used in delivering healthcare to a patient. The module 300 can acquire patient data including the monitored parameters allocated to a given patient from a network and collate the information for storage in a database. The module 300 can be any of a patient monitoring module for acquiring and processing data generated by at least one physiological sensor monitoring a physiological parameter of a patient (e.g., gas measurement, end-tidal carbon dioxide (etCO2), SCIO, patient gas, thermoregulation, blood pressure, heart related measurement, pulse oximetry, respiration, neonatal measurement, ventilation, anesthesia information, incubation information, etc.), a patient treatment module for delivering treatment to the patient (e.g., monitoring fluids administered to the patient and supplying anesthesia to the patient, respectively), a control module, a charging module, a compartment module, a converter module, a transmitter module, a relay module, a battery module, a camera module, a purge module, a robot module, an internal and/or external communication module, a power supply module, a global positioning system (GPS) module, a mobile and/or stationary data transfer module, an output board, a facility module, a Trace Work Area (TWA) control module, an output board, a dock module, an adapter module, a passive treatment module, an active treatment module, etc.

A processor can process signals derived from the module. In the embodiment depicted in FIG. 1, a processor 124 in a (first) monitor 120 can process signals derived from the module 300. In other embodiments, such as the embodiment depicted in FIG. 2, a processor 162 in a monitor mount 160 and/or a processor 142 in another (second) monitor 140 can similarly process signals derived from the module 300. The monitor mount 160 and the monitors 120, 140 communication interface provides bidirectional communication between the corresponding processor and the module via a network.

FIG. 1 is a logical diagram of a monitor 120, and a monitor mount 160 which can detachably secure (or otherwise physically interface with) the monitor 120.

FIG. 2 is a logical diagram of a first monitor 120, a second monitor 140, and a monitor mount 160 which can detachably secure (or otherwise physically interface with) one or both of the first monitor 120 and the second monitor 140.

FIG. 3 illustrates an example system including an exemplary implementation of the first monitor 120, a first exemplary implementation of the second monitor 140, and a first exemplary implementation of the monitor mount 160.

Figure 4:
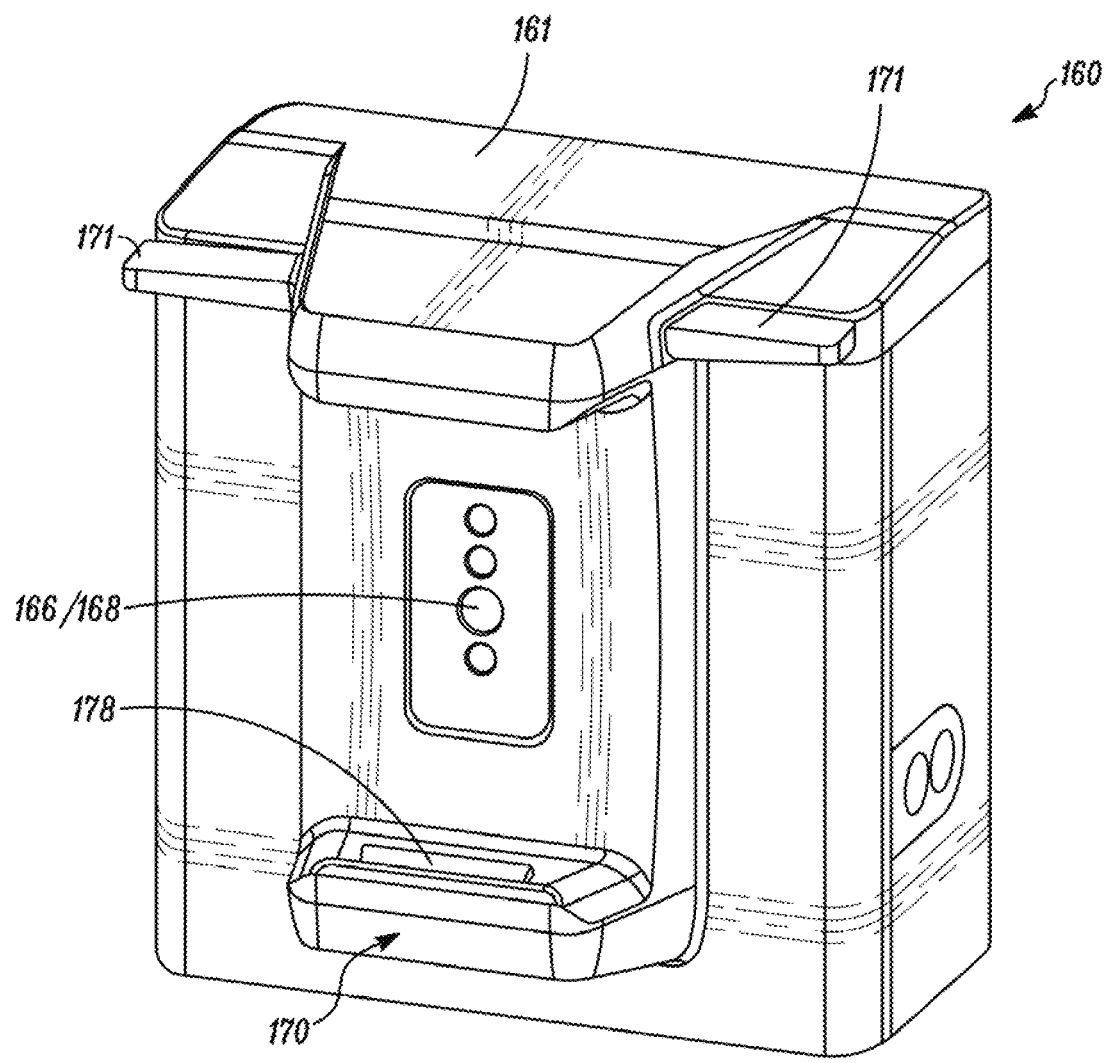
FIG. 4 is a front perspective view of the first exemplary implementation of the monitor mount 160 with a first exemplary implementation of a top portion 161.

FIG. 4 illustrates the first exemplary implementation of the monitor mount 160 with a first exemplary implementation of a top portion 161.

Figure 5:
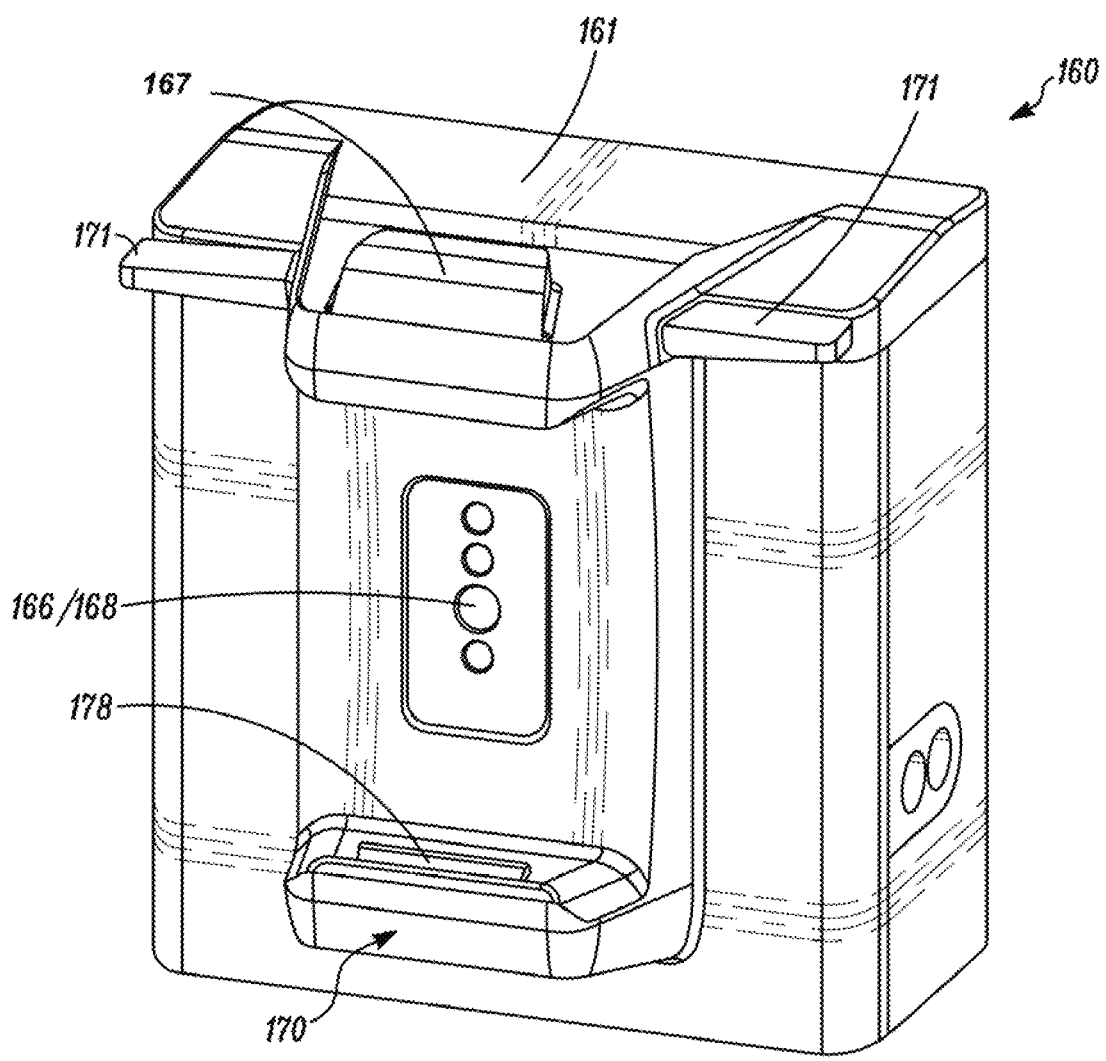
FIG. 5 is a front perspective view of the first exemplary implementation of the monitor mount 160 with a second exemplary implementation of the top portion 161.
Figure 6:
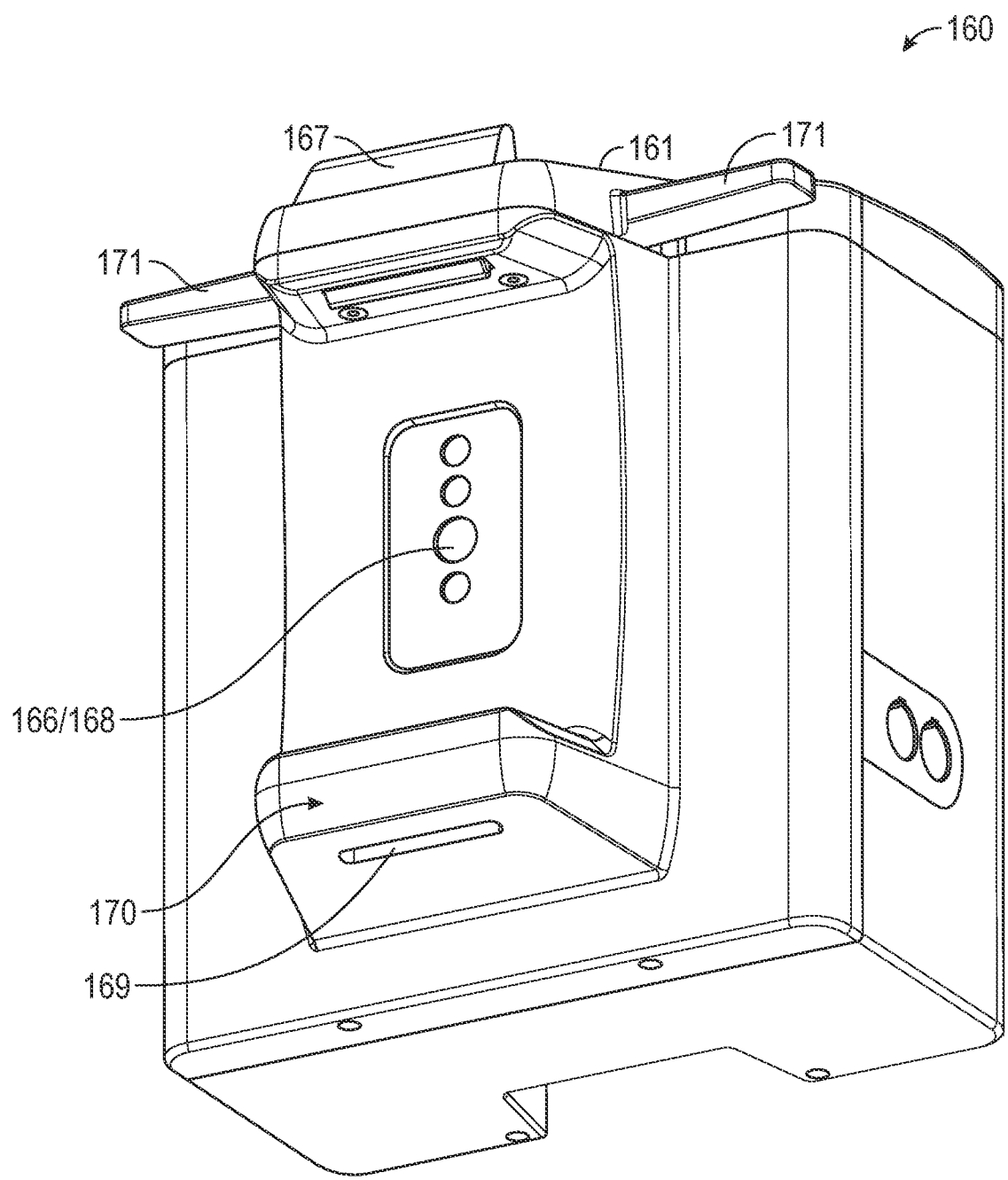
FIG. 6 is a bottom perspective view of the first exemplary implementation of the monitor mount 160 with the second exemplary implementation of the top portion 161.

FIGS. 5 & 6 illustrate the first exemplary implementation of the monitor mount 160 with a second exemplary implementation of the top portion 161.

As will be described in further detail below, the first monitor 120 has a shape and size which differs from that of the second monitor 140. Nonetheless, both of the first monitor 120 and the second monitor 140 are able to be concurrently secured to the monitor mount 160. In addition, while certain configurations are illustrated with regard to the monitor mount 160 and the first monitor 120 and the second monitor 140, it will be appreciated that these illustrations in FIGS. 1-19 are examples and not limiting in nature (unless otherwise specified).

The first monitor 120 can, for example, be a patient monitor that is used to monitor various physiological parameters for a patient 110. With such a variation, the first monitor 120 can include a sensor interface 122 that can be used to connect via wired and/or wireless interfaces to one or more physiological sensors and/or medical devices 112 (e.g., ECG electrodes, SPO2 sensor, blood pressure cuffs, apnea detection sensors, respirators, etc.) associated with the patient 110. The first monitor 120 can include one or more processors 124 (e.g., programmable data processors, etc.) which can execute various instructions stored in memory 130 of the first monitor 120. Various data and graphical user interfaces can be conveyed to a user via an electronic visual display 126 included in the first monitor 120. This information can, for example, relate to the measured physiological parameters of the patient 110 and the like (e.g., blood pressure, cardiac/heart related information, pulse oximetry, respiration information, etc.). Other types of information can also be conveyed by the electronic visual display 126. In some variations, the electronic visual display 126 includes a touch screen interface that allows a user of the first monitor 120 to input data and/or modify the operation of the first monitor 120.

The first monitor 120 can additionally include a communications interface 128 which allows the first monitor 120 to directly or indirectly (via, for example, the monitor mount 160) access one or more computing networks. The communications interface 128 can include, various network cards/interfaces to enable wired and wireless communications with such computing networks. The communications interface 128 can also enable direct (i.e., device-to-device, etc.) communications (i.e., messaging, signal exchange, etc.) such as from the monitor mount 160 to the first monitor 120.

The first monitor 120 can optionally also include a power source and/or conduit 132 that can be used to power the various components of the first monitor 120 (and optionally various components of the second monitor 140 and/or the monitor mount 160). The power source/conduit 132 can include a self-contained power source such as a battery pack and/or the power source/conduit 132 can include an interface to be powered through an electrical outlet (either directly or by way of the second monitor 140 and/or the monitor mount 160). In some variations, the first monitor 120 can only be powered and render information when secured or otherwise connected to one or more of the second monitor 140 and the monitor mount 160.

The first monitor 120 can include a first electrical connector (not shown) configured to connect with a second electrical connector (not shown) of the second monitor 140 via a direct connection. When the first monitor 120 is secured with the second monitor 140, a connection is made by the first electrical connector with the second electrical connector. In some variations, the first monitor 120 may not include the first electrical connector. Instead, the data communication between the first monitor 120 and the second monitor 140 may be wireless (e.g., optical), occurring across the communications interface 128 of the first monitor 120.

The second monitor 140 can include one or more processors 142 (e.g., programmable data processors, etc.) which can execute various instructions stored in memory 144 of the second monitor 140. Various data and graphical user interfaces can be conveyed to the user via an electronic visual display 146 included in the second monitor 140. This information can, for example, relate to the measured physiological parameters of the patient 110 and the like (e.g., blood pressure, heart related information, pulse oximetry, respiration information, thermoregulation, neonatal information, ventilator information, anesthesia information, incubation information, etc.) as received from the first monitor 120. Other types of information can also be conveyed by the electronic visual display 146. In some variations, the electronic visual display 146 includes a touch screen interface that allows a user of the second monitor 140 to input data and/or modify the operation of the second monitor 140.

The second monitor 140 can additionally include a communications interface 148 which allows the second monitor 140 to directly or indirectly (via, for example, the first monitor 120 and/or the monitor mount 160) access one or more computing networks. The communications interface 148 can include various network cards/interfaces to enable wired and wireless communications with such computing networks. The communications interface 148 can also enable direct (i.e., device-to-device, etc.) communications (i.e., messaging, signal exchange, etc.) such as from the monitor mount 160 to the second monitor 140 and the first monitor 120 to the second monitor 140.

The second monitor 140 can optionally also include a power source and/or conduit 150 that can be used to power the various components of the second monitor 140 (and optionally various components of the first monitor 120). The power source/conduit 150 can include a self-contained power source such as a battery pack and/or the power source/conduit 150 can include an interface to be powered through an electrical outlet (either directly or by way of the first monitor 120 and/or the monitor mount 160). In some variations, the second monitor 140 can only be powered and render information when secured or otherwise connected to one or more of the first monitor 120 and the monitor mount 160.

Figure 15:
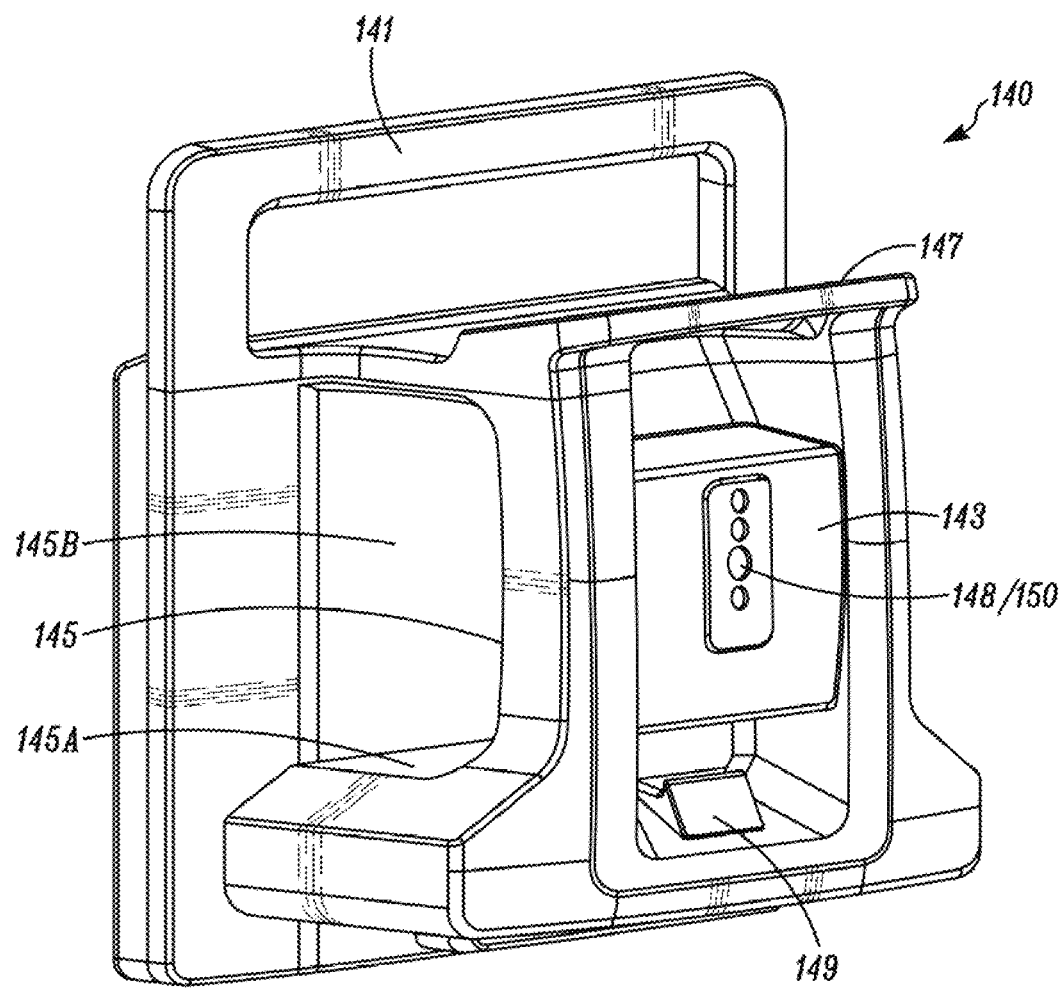
FIG. 15 is a rear perspective view of the first exemplary implementation of the second monitor 140.

The second monitor 140 can include a second coupling 145 which is configured to detachably secure the first monitor 120. In some variations, the second coupling 145 may be positioned in a receptacle 145B (as shown in FIG. 15) of the second monitor 140. The receptacle 145B may be defined in a lateral direction of the second monitor 140 and have open side portions for receiving the first monitor 120. For example, the user can visually confirm the location of the second coupling 145 and transversely insert the first monitor 120 into the second monitor 140. The first monitor 120 may include one or more of a groove, a slit, an aperture, a rib, a wall portion, a ridge, an abutment, or the like for facilitating the transverse insertion and/or removal of the first monitor 120 into the receptacle 145B of the second monitor 140.

The monitor mount 160 can include one or more processors 162 (e.g., programmable data processors, etc.) which can execute various instructions stored in memory 164 of the monitor mount 160. The monitor mount 160 can additionally include a communications interface 166 which allows the monitor mount 160 to directly or indirectly access one or more computing networks. The communications interface 166 can include various network cards/interfaces to enable wired and wireless communications with such computing networks. The communications interface 166 can also enable direct (i.e., device-to-device, etc.) communications (i.e., messaging, signal exchange, etc.) such as with the first monitor 120 and/or the second monitor 140.

The monitor mount 160 can optionally also include a power source and/or conduit 168 that can be used to power the various components of the monitor mount 160 and/or the first monitor 120 and/or the second monitor 140 when secured to the monitor mount 160. The power source/conduit 168 can include a self-contained power source such as a battery pack and/or the power source/conduit 168 can include an interface to be powered through an electrical outlet.

Any of the processors 124, 142, 162 may acquire data from any of the monitor mount 160 and one or more of the monitors 120, 140 and store the acquired data in a memory and, upon connection of the monitor mount 160 and one or more of the monitors 120, 140, transfer the data stored in the memory to the monitor mount 160 or one or more of the monitors 120, 140. The data may include any of patient identification data including information identifying a patient; patient parameter data representing at least one type of patient parameter being monitored; and device configuration data including information associated with configuration settings for the monitor mount 160 and/or the one or more monitors 120, 140.

The monitor mount 160 can optionally also include any mounting interface, such as a VESA mounting interface 165 (e.g., a 75 mm or 100 mm square pattern) for mounting the monitor mount at the bedside, from the ceiling, on a wall of the room, or even outside the room for isolation purposes.

The monitor mount 160 can optionally also include an interface configured to receive a connector of a cable or wired connection for connecting a module, a monitor, other external unit, or the like.

In some variations, the one or more processors 162 and the memory 164 are omitted such that the monitor mount 160 provides only physical support and optionally a power source.

The monitor mount 160 has a shape and size which allows the monitor mount 160 to detachably secure both of the first monitor 120 and the second monitor 140 such that the respective monitors 120 and 140 can be removed by the user when desired.

The monitor mount 160 can include a first coupling 170 to allow the first monitor 120 and/or second monitor 140 to be secured to the monitor mount 160. The monitor mount 160 is able to secure each of the first monitor 120 and the second monitor 140 individually or both of the first monitor 120 and the second monitor 140 concurrently. In other words, the first coupling 170 is configured to accept either the first monitor 120 or the second monitor 140 such that the monitor mount 160 is configured to mount the first monitor 120 alone, the second monitor 140 alone, or a combination of the first monitor 120 and the second monitor 140. The first coupling 170 can include any mechanical attachment means such as a ledge, a rail, a rib, an abutment, and the like, or any combination thereof. The first coupling 170 can additionally include different securing mechanisms including magnetic and/or electromagnetic locking mechanisms which cause the first monitor 120 to selectively be secured to the monitor mount 160. In some variations, the first monitor 120 can be mounted to and removed from the front face of the monitor mount 160.

The positioning of the first monitor 120 when secured to the monitor mount 160 can be such that the communications interface 128 on the first monitor 120 aligns with the communications interface 166 of the monitor mount 160 to allow, for example, a direct connection (e.g., electrical connection). In other variations, the communications interface 128 of the first monitor 120 exchanges data with the communications interface 166 of the monitor mount 160 wirelessly (via, for example, optical communication by way of respective optical windows on the first monitor 120 and the monitor mount 160). The communications interface 128 of the first monitor 120 may be located on the first back portion 123 of the first monitor 120.

The positioning of the first monitor 120, when secured to the monitor mount 160, can also align the power source/conduit 132 of the first monitor 120 to be coupled to the power source conduit 168 of the monitor mount 160 which causes the monitor mount 160 to power the first monitor 120.

The second exemplary implementation of the top portion 161 can include a support portion 167 to allow the second monitor 140 to be secured to the monitor mount 160. The support portion 167 can include any mechanical attachment means such as a ledge, a rail, a rib, an abutment, and the like, or any combination thereof. The positioning of the second monitor 140 when secured to the monitor mount 160 can be such that the communications interface 148 on the second monitor 140 aligns with the communications interface 166 of the monitor mount 160 to allow, for example, a direct connection (e.g., electrical connection). In other variations, the communications interface 148 of the second monitor 140 exchanges data with the communications interface 166 of the monitor mount 160 wirelessly (via, for example, optical communication by way of respective optical windows on the second monitor 140 and the monitor mount 160). The communications interface 148 of the second monitor 140 may be located on a second back portion 143 of the second monitor 140.

As shown in FIGS. 3, 5 & 6, the support portion 167 can enable hanging or suspension of a hook portion 147 of the second monitor 140 from the monitor mount 160 by providing any mechanical attachment means such as a ledge, a rail, a rib, an abutment, and the like, or any combination thereof extending laterally from the top portion 161 of the monitor mount 160. This feature of the support portion 167 can support and/or disperse the weight of the second monitor 140 during positioning of the second monitor 140. For example, a user attempting to position the second monitor 140 within the monitor mount 160 can hang or suspend the hook portion 147 of the second monitor 140 from the support portion 167 during the positioning while attaching the second back portion 143 of the second monitor 140 to the first coupling 170.

The positioning of the second monitor 140, when secured to the monitor mount 160, can also align the power source 7 conduit 150 of the second monitor 140 to be coupled to the power source/conduit 168 of the monitor mount 160 which causes the monitor mount 160 to power the second monitor 140 or vice-versa. In some variations, the positioning of the second monitor 140 when secured to the monitor mount 160 and/or when the first monitor 120 is also secured to the monitor mount 160 can also align the power source/conduit 150 of the second monitor 140 to be coupled to the power source/conduit 132 of the first monitor 120 (which in turn is connected to the power source/conduit 168 of the monitor mount 160) which causes the first monitor 120 to power the second monitor 140.

FIG. 3 is an exploded perspective view that shows the relationship among the first monitor 120, the first exemplary implementation of the second monitor 140, and the first exemplary implementation of the monitor mount 160. The first back portion 123 of the first monitor 120 or the second back portion 143 of the second monitor 140 can be detachably secured to the first coupling 170. The first monitor 120 can also be detachably secured to the second coupling 145 of the second monitor 140. The second back portion 143 of the second monitor 140 is detachably secured to the first coupling 170 of the monitor mount 160, the hook portion 147 is suspended from the support portion 167, and the first monitor 120 is detachably secured to the second coupling 145 of the second monitor 140. In some variations, a portion such as a back portion of the second monitor 140 can surround/obscure at least a portion of the first monitor 120; such portion of the first monitor 120 may include some or all of the electronic visual display 126 of the first monitor 120. The first monitor 120 can be removed from the monitor mount 160 independently of the second monitor 140 (for example, with reference to FIG. 3, by being removed transversely from the monitor mount 160). The second monitor 140 can be arranged to allow left side and/or right side transverse removal of the first monitor 120 from the second monitor 140.

In still other variations, the second monitor 140 with the first monitor 120 disposed therein can be removed from the monitor mount 160. Stated differently, the combination of the first monitor 120 and the second monitor 140 can together be detached from the monitor mount 160. In some variations, the second monitor 140 can have a shape and size to completely envelop and secure the first monitor 120 within the receptacle 145B. The first monitor 120 can be secured and interface within the second coupling 145 in the receptacle 145B of the second monitor 140. In some variations, when the first monitor 120 is mounted within the receptacle 145B of the second monitor 140, the communications interface 148 (e.g., optical communications interface), and optionally the power source/conduit 150, on the second monitor 140 provide data communications with, and optionally power to, the first monitor 120 via the communications interface 128 (e.g., optical communications interface), and optionally the power source/conduit 132, on the first monitor 120 within the receptacle 145B.

In further variations, the first monitor 120 may be detachably secured in the monitor mount 160 without the second monitor 140 being present. Accordingly, the first back portion 123 of the first monitor 120 may be detachably secured to the first coupling 170.

For example, with such an arrangement, data that otherwise would have been displayed by the electronic visual display 126 of the first monitor 120 can be displayed by the electronic visual display 146 of the second monitor 140.

Therefore, the monitor mount 160 of the present disclosure is capable of mixed use with monitors 120, 140 having different sizes which are interoperable with the same controller and the same user interface, and which can be universally docked to the monitor mount 160.

FIG. 4 is a front perspective view that shows the first exemplary implementation of the monitor mount 160 with a first exemplary implementation of the top portion 161. The communications interface 166 and the power/source conduit 168 can be positioned intermediate of the first coupling 170 so that the first monitor 120 or the second monitor 140 may interface therewith. In some variations, communications interface 166 can be a wireless (e.g., optical) interface providing wireless (e.g., optical) communications between the monitor mount 160 and the first monitor 120, between the monitor mount 160 and the second monitor 140, and/or between the first monitor 120 and the second monitor 140 coupled together. Additional wireless communication protocols that be implemented may include one or more of Bluetooth, Bluetooth Low Energy, Zigbee, Z-wave, 2G/3G/4G/5G, NFC (Near Field Communication), and Wi-Fi, to list a few examples.

FIG. 5 is a front perspective view that shows the first exemplary implementation of the monitor mount 160 with a second exemplary implementation of the top portion 161. As illustrated in FIG. 5, the monitor mount 160 includes the first coupling 170 and the support portion 167.

FIG. 6 is a bottom perspective view that shows the first exemplary implementation of the monitor mount 160 with the second exemplary implementation of the top portion 161. As illustrated in FIG. 6, the monitor mount 160 includes the first coupling 170 and the support portion 167. In the embodiment shown in FIG. 6, a slot 169 is defined in an underside of the coupling 170.

Figure 7:
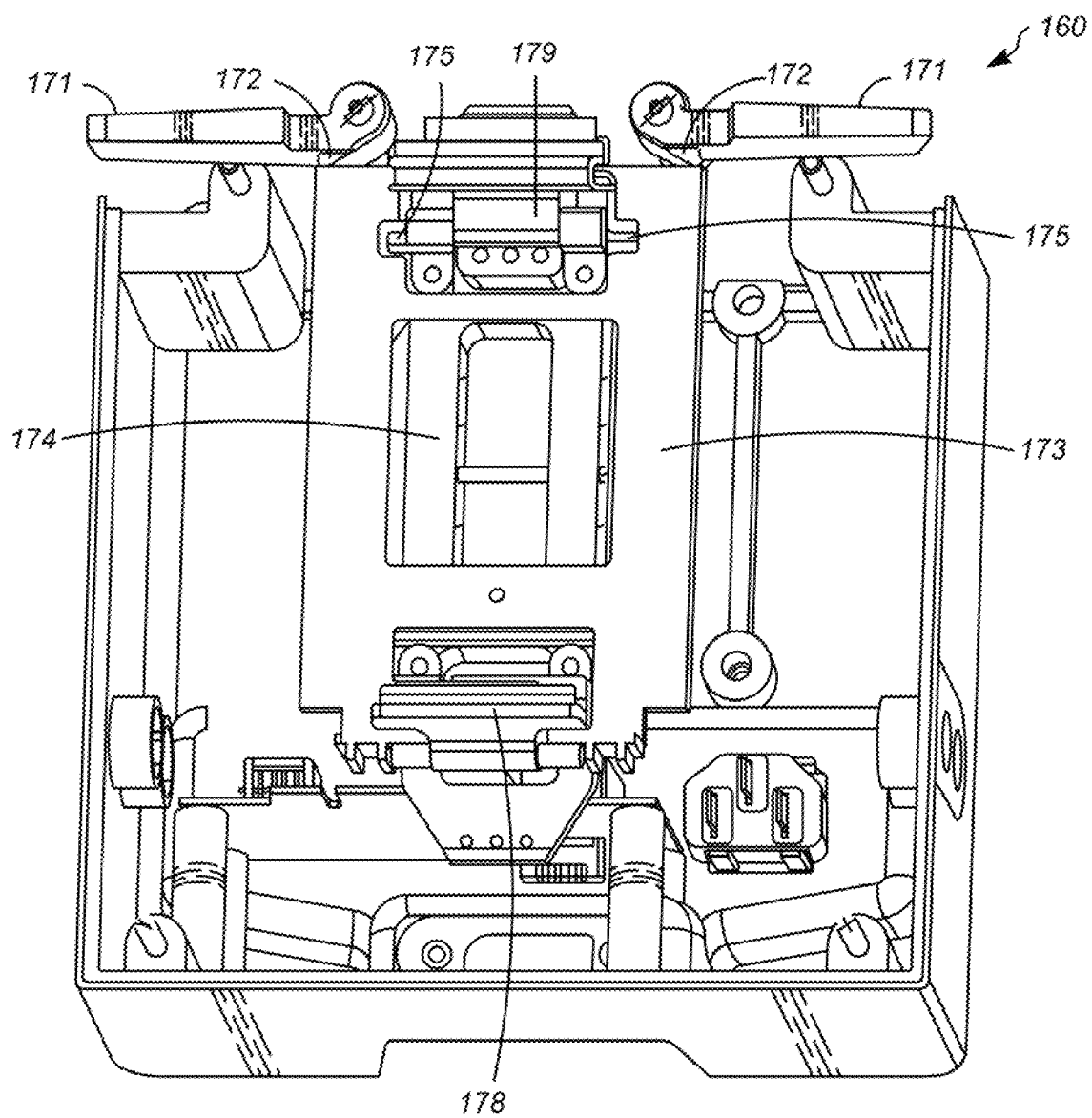
FIG. 7 is a front perspective view of the first exemplary implementation of the monitor mount 160 with a front face thereof removed.

FIG. 7 is a front perspective view of the first exemplary implementation of the monitor mount 160 with a front face thereof removed.

Figure 8:
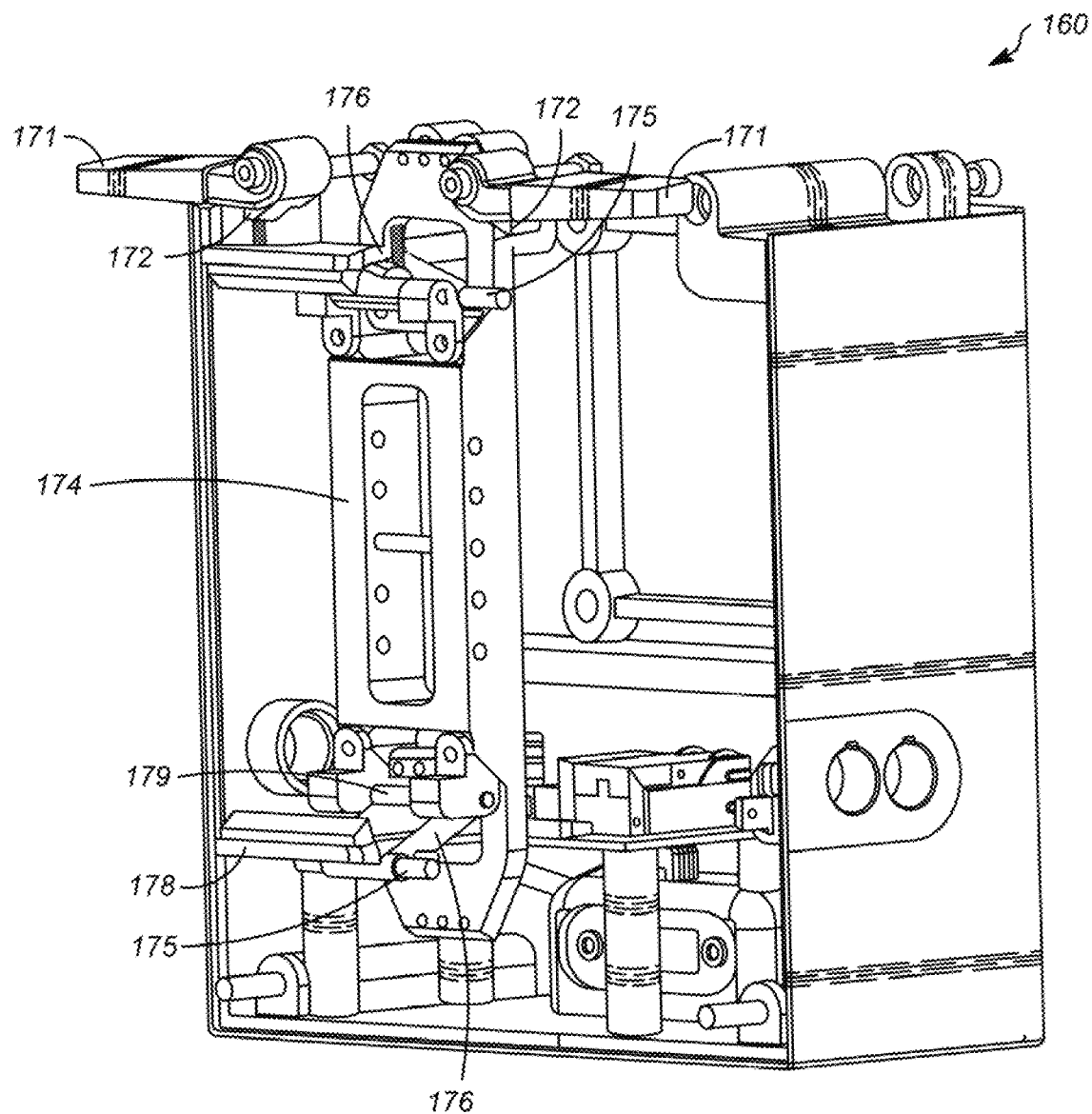
FIG. 8 is a side perspective view of the first exemplary implementation of the monitor mount 160 with a front face and a slider 173 thereof removed.

FIG. 8 is a side perspective view of the first exemplary implementation of the monitor mount 160 with a front face and a slider 173 thereof removed. These figures illustrate, for example, how the actuators 171, 172, slide bars 173 and/or chassis 174, (and other components) are installed within the monitor mount 160.

As shown in FIGS. 4-8, the first exemplary implementation of the monitor mount 160 may comprise the coupling 170 configured to detachably secure a monitor 120 and/or 140 to the monitor mount 160, and a release mechanism configured to disengage the coupling 170 so as to release the monitor 120 and/or 140 from the monitor mount 160. The release mechanism may include at least one actuator 171, at least one cam 172, and a slider 173. The at least one cam 172 may be positioned on an underside of the at least one actuator 171. In some variations, the at least one cam 172 and the at least one actuator 171 may be formed as a single unit. The at least one cam 172 may be attached to the at least one actuator 171, configured to be rotated by the at least one actuator 171, and configured to cause the slider 173 to slide. The slider 173 may be linked to the coupling 170, and configured to disengage the coupling 170 upon sliding. In the embodiments shown in FIGS. 4-8, the at least one actuator 171 is a lever. In the embodiments shown in FIGS. 4-8, two actuators 171 (i.e., a first actuator and a second actuator) are provided on respective left and right sides of the monitor mount 160 and two cams 172 (i.e., a first cam and a second cam) are positioned on respective undersides of the two actuators 171. The slider 173 may be configured to slide based on activation of the first actuator 171 and/or the second actuator 171. In other words, the slider 173 may be configured to slide based on activation of either the first actuator 171 or the second actuator 171 such that the slider 173 is configured to slide based on activation of the first actuator 171 individually, activation of the second actuator 171 individually, or activation of the first actuator 171 and the second actuator 171 simultaneously.

In some variations, the coupling 170 includes at least one arm 176, at least one latch 178 extending from the at least one arm 176, at least one pin 175 extending from the at least one arm 176, and at least one hinge 179. The at least one latch 178 may extend from, for example, a top portion of the at least one arm 176. The at least one pin 175 may extend from, for example, a side portion of the at least one arm 176. In the implementation shown in FIGS. 7 & 8, the coupling 170 includes two arms 176 (i.e., a first arm and a second arm) provided on respective top and bottom sides of the monitor mount 160. The release mechanism may also include a chassis 174 for supporting the coupling 170 and the slider 173.

In the implementations shown in FIGS. 4-8, the monitor mount 160 may additionally include a top portion 161 for supporting the actuators 171 and the cams 172. For example, each of the actuators 171 may be attached to the top portion 161 via a shaft such that the actuator 171 is rotatable with respect to the top portion 161.

Furthermore, the chassis 174 may extend behind and alongside a front face of the monitor mount 160. Each of the arms 176 may be attached to the chassis 174 via a hinge 179 such that the arm 176 is rotatable with respect to the chassis 174. The slider 173 may be configured to disengage the latches 178 upon sliding. In the embodiment shown in FIGS. 7 & 8, the slider 173 may be attached to the pins 175 of the arms 176 such that, upon sliding of the slider 173, the pins 175 are displaced so as to rotate the arms 176 outwardly such that the latches 178 are disengaged and the monitor 120, 140 can be released from the monitor mount 160. The latches 178 may be biased by springs (not shown). In the embodiment shown in FIGS. 7 & 8, the pins 175 of the arms 176 may be positioned inwardly of the latches 178. Such a configuration causes the latches 178 to grip more tightly to prevent the accidental release of the monitor 120, 140. In the embodiment shown in FIGS. 7 & 8, the pins 175 of the first arm 176 may be closer to the chassis 174 than the pins of the second arm 176. Such a configuration allows the arms 176 to move equal amounts upon sliding of the slider 173 and results in different pivot lengths of the arms 176 so as to enable opposite movement of the arms 176. By configuring the monitor mount 160 as described above, a low profile can be obtained and a space between the monitor 120, 140 and the monitor mount 160 can be minimized when the monitor 120, 140 is detachably secured to the monitor mount 160.

The monitor mount 160 may be configured to receive interchangeable first and second top portions 161 for accommodating monitors of different types. The monitors of different types may include monitors of different sizes such as monitors 120, 140. In other words, a first top portion 161 as shown in FIG. 4 may be implemented such that the monitor mount 160 is able to accommodate a first monitor 120. As shown in FIGS. 5 & 6, a second top portion 161 may be implemented such that the monitor mount 160 is able to accommodate a second monitor 140 or a combination of a first monitor 120 and a second monitor 140. Any of the top portions 161 may be contoured so as to facilitate thermal mitigation.

Figure 9:
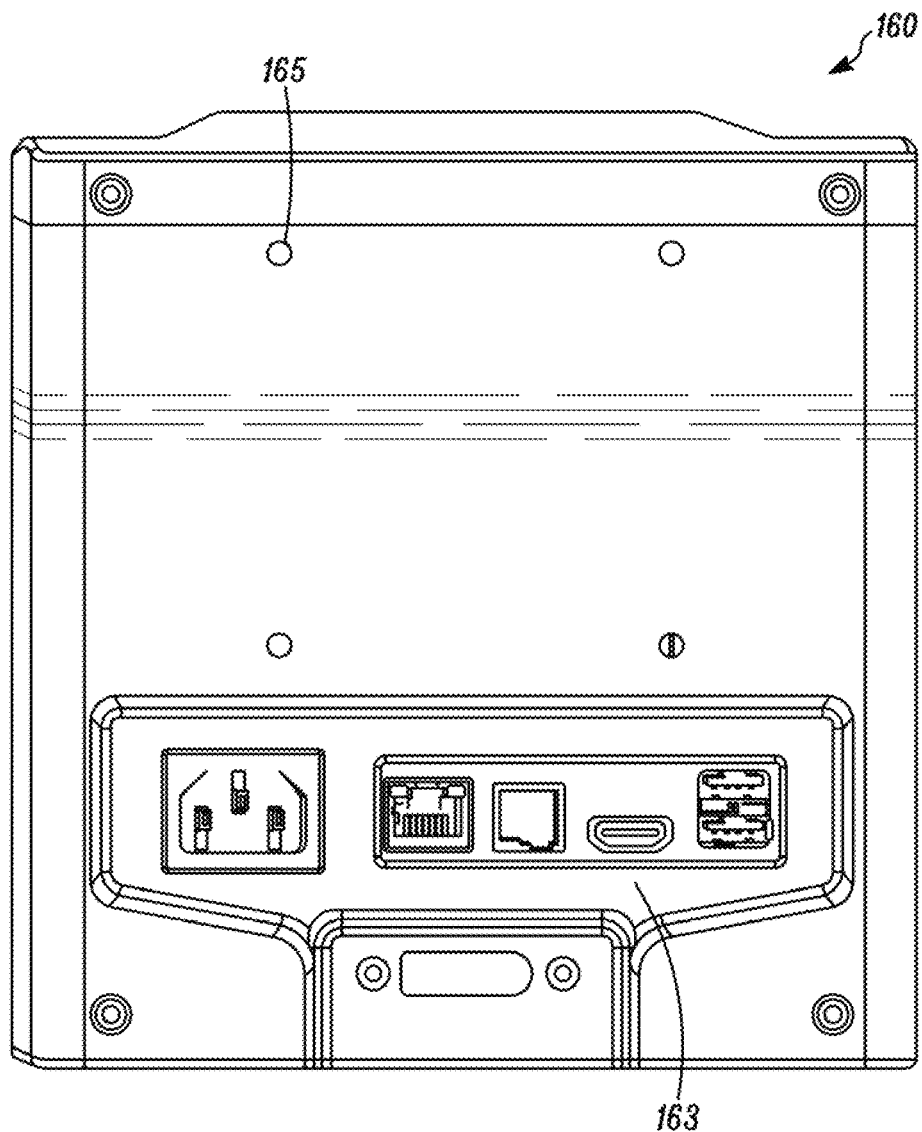
FIG. 9 is a rear view of the first exemplary implementation of the monitor mount 160.

FIG. 9 is a rear perspective view that shows the first exemplary implementation of the monitor mount 160. The monitor mount 160 may include a cutout 163 on a back surface thereof for permitting a flow of fluid. In this way, the fluid is directed away from electrical connections of the monitor mount 160 and damage thereto is prevented.

Figure 10:
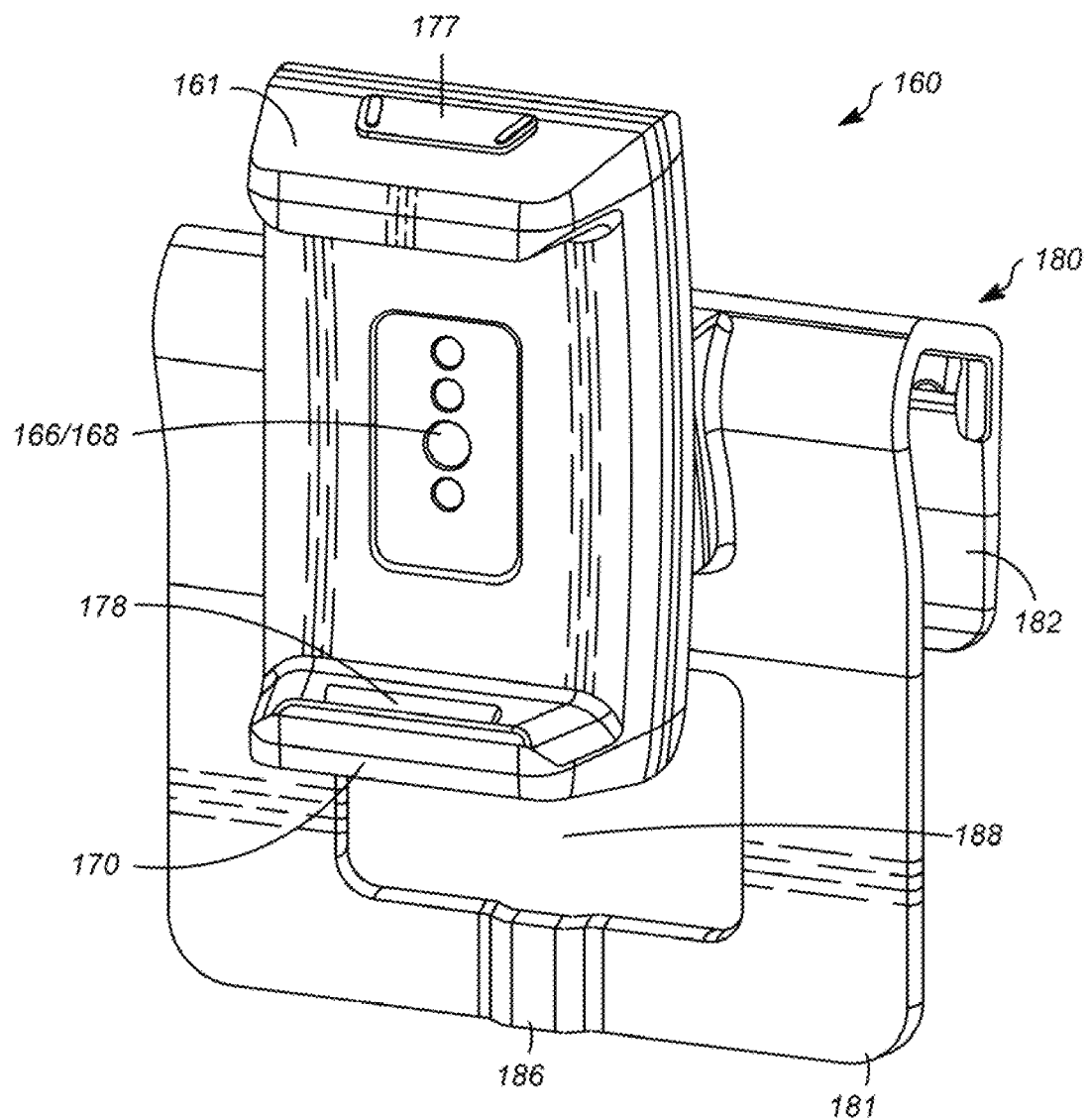
FIG. 10 is a front perspective view of a second exemplary implementation of the monitor mount 160 with a clip 180.
Figure 11:
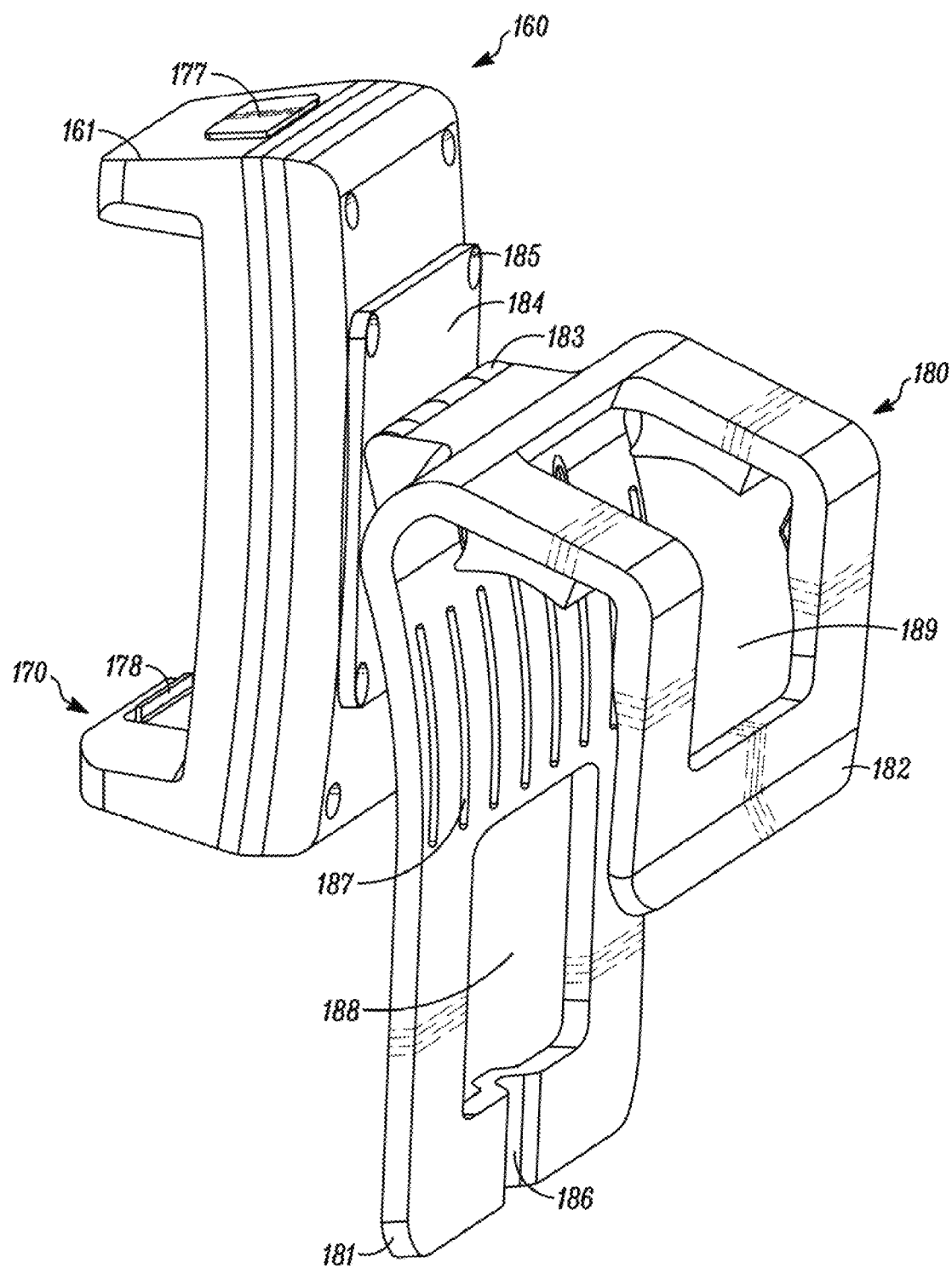
FIG. 11 is a side perspective view of the second exemplary implementation of the monitor mount 160 with the clip 180.

FIGS. 10 & 11 show a second exemplary implementation of the monitor mount 160 for detachably securing a device (e.g., monitor, rack, module, etc.) to a support structure (e.g., bed, stretcher, gurney rail, IV pole, ambulance bar, monitor mount, workstation, stand, etc.). In the implementation shown in FIGS. 10 & 11, the actuator 177 is a push button (as an alternative to the lever shown in FIGS. 4-8). Pressure applied to the push button causes the slider 173 to slide and disengage the latches 178 as explained above.

The second exemplary implementation of the monitor mount 160 may include a mounting plate 184 attached to a back surface of the monitor mount 160 and a clip 180 configured to detachably secure the monitor mount 160 to the support structure. The clip 180 is important for clinical workflow challenges with transport and moving the patient between care areas (e.g., from an Emergency Department to Radiology or from a CT scan to the OR). The monitor 120, 140 can be attached to an IV pole, bed rail, etc., using the clip 180 so that the monitor 120, 140 does not fall or get wrapped in bedsheets on transport. The clip 180 may be portable and can be used with various types of connectors to patient monitoring devices, portable structures, or stationary structures.

The clip 180 may allow for long-term or short-term attachment of a monitor to another structure. A short-term attachment fitting allows a user to mount the clip 180 to a difficult location on a structure and then interchange the monitor as needed. Conversely, a long-term attachment fitting allows for a robust connection, in which the clip position can be changed as needed without excessive concern from the user about the stability of the location of the monitor. The clip 180 can allow the monitor 120, 140 to rotate with respect to the clip 180 affixed to a rail, pole, or other structure. Though this rotation is described below in discrete increments of 90°, this rotation can include increments of less than 90°, greater than 90°, or an arbitrary rotation. One of the advantages of the ability to rotate the monitor 120, 140 relative to the clip 180 is that cable and cord routing from the monitor 120, 140 to the patient can be simplified. Another advantage of this ability to rotate the monitor 120, 140 relative to the clip 180 is that the assembly can adapt to more locations around a patient's bed.

Accordingly, the clip 180 can attach to a bed rail, a shelf or ledge near a patient's bed, or onto a rack or pole used for other equipment that is near a patient, and the monitor 120, 140 can be turned to a convenient orientation about the clip 180 because of this ability to rotate. Accordingly, the monitor 120, 140 can be accommodated to each patient's environment. In other words, the clip 180 may be attached to the mounting plate 184 by a hinge 183 such that the mounting plate 184 is rotatable with respect to the clip 180. For example, the mounting plate 184 is rotatable across 270° with respect to the clip 180 such that the mounting plate 184 can be positioned in a vertical orientation and a horizontal orientation. The mounting plate 184 can include any mounting interface such as a VESA mounting interface 185.

The clip 180 may define a hook including a base plate 181 on a first side of the clip 180 and a back plate 182 on a second side of the clip 180. In some variations, a length of the base plate 181 may be greater than a length of the back plate 182. The back plate 182 may be flexible so as to facilitate mounting of the monitor mount 160 on the support structure. The base plate 181 and back plate 182 have ergonomic features that can allow a user to better utilize the clip 180. For example, the base plate 181 may further include a grip portion 187 for gripping a vertical member (not shown) of the support structure. For example, the grip portion 187 may be comprised of an elastomeric material. The base plate 181 may also include a notch 186 for receiving the vertical member of the support structure. The notch 186 prevents rotation of the monitor mount 160 around the vertical member of the support structure. Furthermore, a bottom edge of the base plate 181 may be configured to be supported on a horizontal member (not shown) of the support structure. Such a configuration allows for a robust connection between the monitor mount 160 and the support structure. In some variations, the base plate 181 may include an opening 188 defined therein and/or the back plate 182 may include an opening 189 defined therein. The openings 188, 189 may serve to reduce the overall mass of the clip 180, thereby improving the portability of the clip 180. In some variations, at least one of the openings 188, 189 may be square. In other variations, the openings 188, 189 may be arcuate. In the embodiment shown in FIGS. 10 & 11, electrical connections may be omitted such that the monitor mount 160 provides only physical support. Therefore, the second exemplary implementation of the monitor mount 160 enables a user to quickly and easily secure and remove a monitor from a support structure.

Figure 13A:
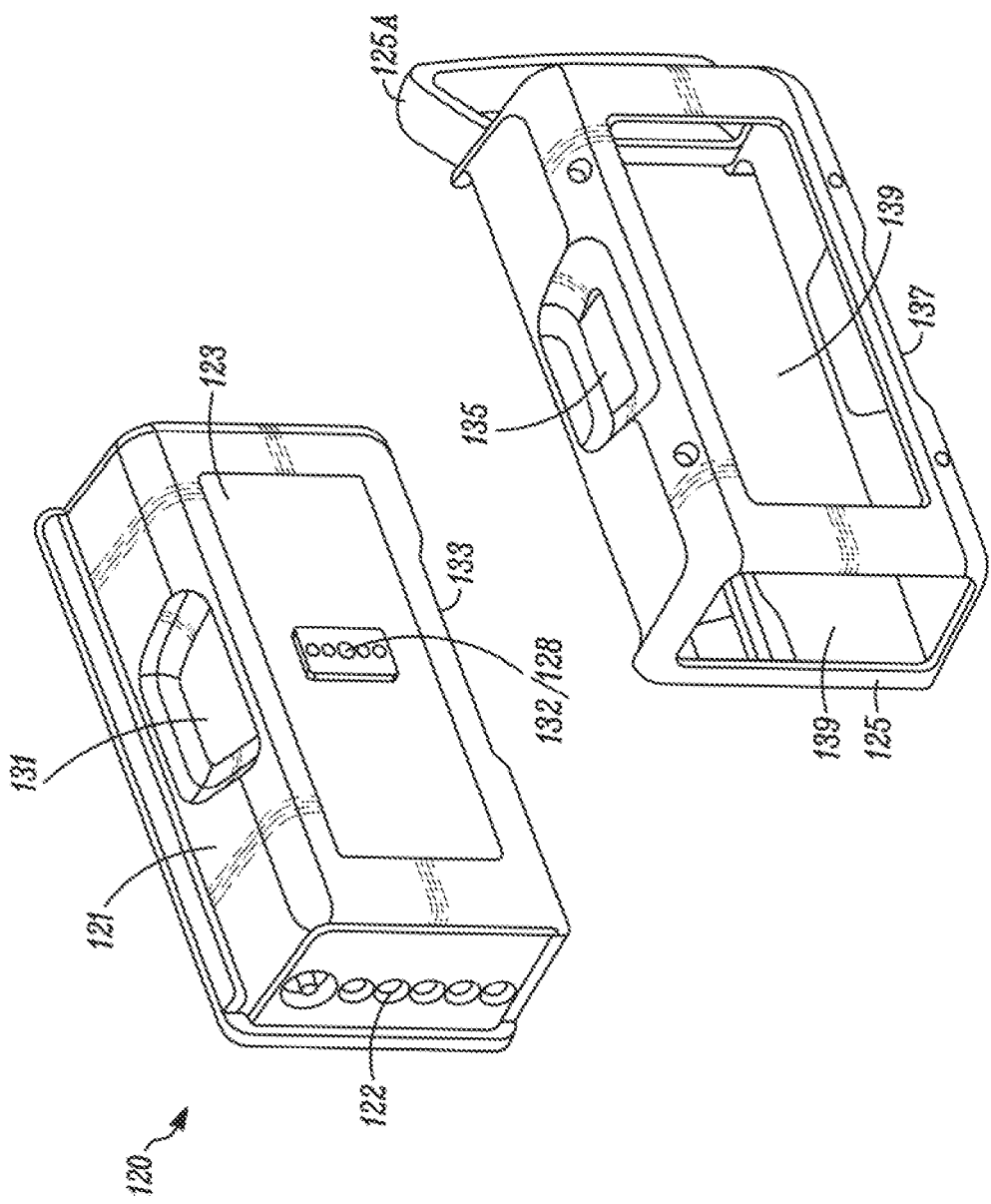
FIG. 13A is an exploded rear perspective view of the exemplary implementation of the monitor 120.

FIGS. 12-13O show an exemplary implementation of the first monitor 120. As illustrated in FIGS. 13A-13C, the first monitor 120 has a case 121, the sensor interface 122, the first back portion 123, a cover 125, the communications interface 128, and the power source and/or conduit 132. The case 121 may be configured to hold an electronic visual display 126, and the cover 125 may be configured to be detachably secured to the case 121. For example, the cover 125 may be configured to be detachably secured to a back portion of the case 121 and may also surround the back portion of the case 121. In some variations, the cover 125 may be detachably secured to the case 121 via at least one fastener (not shown). For example, the at least one fastener may be a screw. The cover 125 may extend across a full width of the monitor 120 in a lateral direction. The cover 125 may be modular such that it can be reversibly secured to the case 121 in multiple different orientations of the case 121. Such orientations may be opposite to one another.

As shown in FIGS. 13A-13C, the cover 125 may be symmetrical with respect to a longitudinal center axis of the monitor 120. In addition, an interface between the cover 125 and the case 121 may be symmetrical with respect to a longitudinal center axis (e.g., X-axis) of the monitor 120 and a lateral center axis (e.g., Y-axis) of the monitor 120. The symmetrical design thereby enables the provision of, for example, both left-hand and right-hand configurations using a single cover 125. As shown in FIG. 13A, the cover 125 may include an opening 139 defined in at least one of a side portion of the cover 125 or a back portion of the cover 125. The opening 139 provides access for connectors and user interface areas regardless of the orientation in which the cover 125 is positioned. The opening 139 can also expose a product label on the back portion 123 of the case 121

In some variations, the cover 125 may include a handle 125A extending from, for example, a side portion of the cover 125. The cover 125 and the handle 125A may be formed as a single unit. The handle 125A may be in line with a perimeter of the cover 125. Alternatively, the handle 125A may be at an oblique angle with respect to the perimeter of the cover 125. Such an oblique angle may optimize the center of gravity of the monitor 120 and provide a clearance for connectors for a sensor interface 122 which may be located on either lateral side of the monitor 120 such that interference of associated cables for the connectors is avoided. The handle 125A may be curved or arcuate. In some variations, no handles 125A may be included or multiple handles 125A may be included on respective sides of the cover 125. In other variations, one handle 125A may be included; for example, on a side of the cover 125 corresponding to a side of the monitor 120 in which a battery (not shown) is located.

In addition, the case 121 may include a first recess 131 and a second recess 133 together defining either a grip portion for a user's fingers and/or a mount portion for mounting the cover 125 to the case 121. For example, the first recess 131 may be defined in a top portion of the case 121 and the second recess 133 may be defined in a bottom portion of the case 121. Similarly, the cover 125 may include a first recess 135 and a second recess 137 together defining a mount portion configured to physically interface with the coupling 170. For example, the first recess 135 may be defined in a top portion of the cover 125 and the second recess 137 may be defined in a bottom portion of the cover 125.

A front side of the monitor 120 may have a maximum surface area of the sides of the monitor 120, may provide any one or more of a user interface, an alarm bar, a speaker opening, buttons 129 and/or cover glass. The buttons 129 may be flush with the front side of the monitor 120 so as to prevent accidental actuation. In some variations, the case 121 and/or the cover 125 may be comprised of plastic. The monitor 120 can be adapted for ambulance, air medical services, shock-susceptible, vibration-susceptible, and/or military specification applications where a more robust monitor configuration is appropriate. The monitor 120 is versatile, contributes to a high level of hygiene, is easily cleanable, is compact in size, reduces costs, features easy assembly, and is quickly repairable. The monitor 120 is also resistant to shocks or drops and water ingress.

Figure 14:
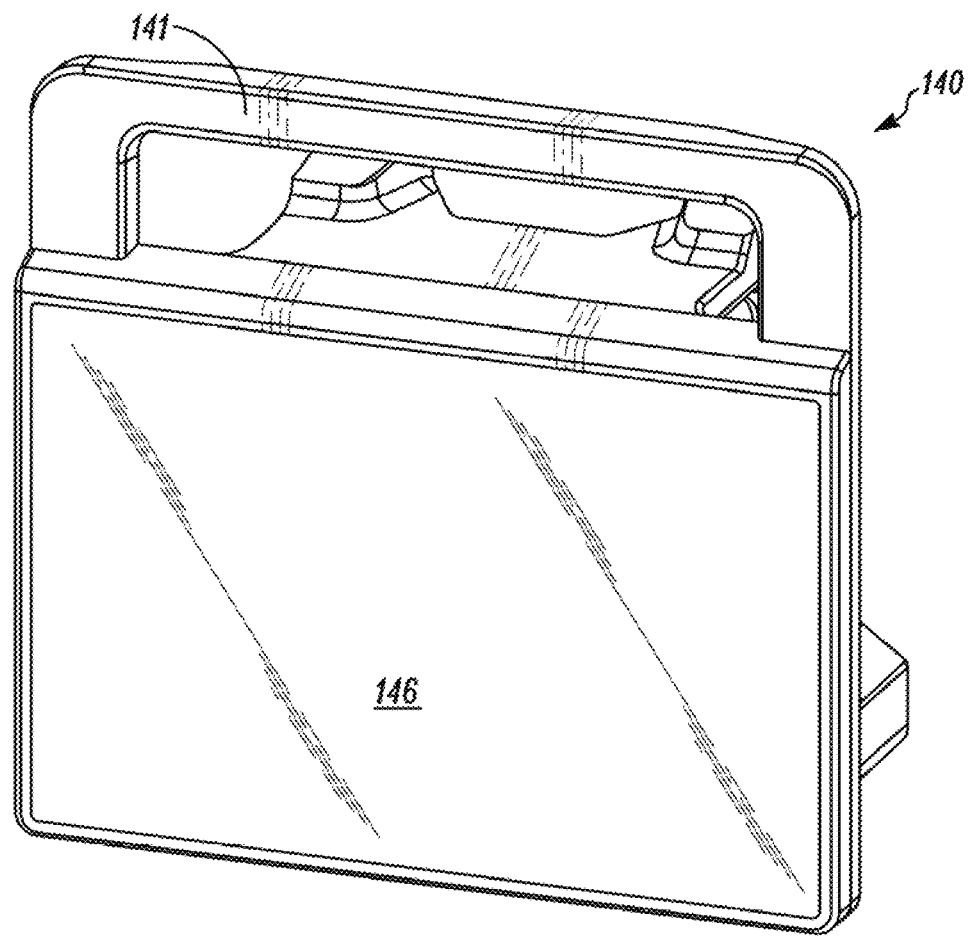
FIG. 14 is a front perspective view of a first exemplary implementation of the second monitor 140.

FIG. 14 is a front perspective view of a first exemplary implementation of the second monitor 140. As illustrated in FIG. 14, the second monitor 140 has a handle 141, and an electronic visual display 146.

FIG. 15 is a rear perspective view of the first exemplary implementation of the second monitor 140. As illustrated in FIG. 15, the second monitor 140 has a handle 141, a second back portion 143, a second coupling 145, a hook portion 147, a communications interface 148, and a power source and/or conduit 150. The hook portion 147 can facilitate the detachable securing of the second monitor 140 to the support portion 167 (as shown in FIGS. 3, 5 & 6) and/or the first coupling 170. The second coupling 145 can have one or more guiding surfaces 145A for facilitating the transverse insertion and/or removal of the first monitor 120 into the receptacle 145B of the second monitor 140. The first exemplary implementation of the second monitor 140 may further include a latch 149. In some variations, the latch 149 can facilitate the detachable securing of the second monitor 140 to the first coupling 170 by fitting into a slot 169 defined in an underside of the coupling 170 (as shown in FIG. 6). The latch 149 may be spring-loaded such that the latch 149 is biased into the slot 169 (shown in FIG. 6) when the second monitor 140 is being detachably secured to the monitor mount 160. For example, the hook portion 147 may be located on a top side of the back portion 143 and the latch 149 may be located on a bottom side of the back portion 143.

Figure 16:
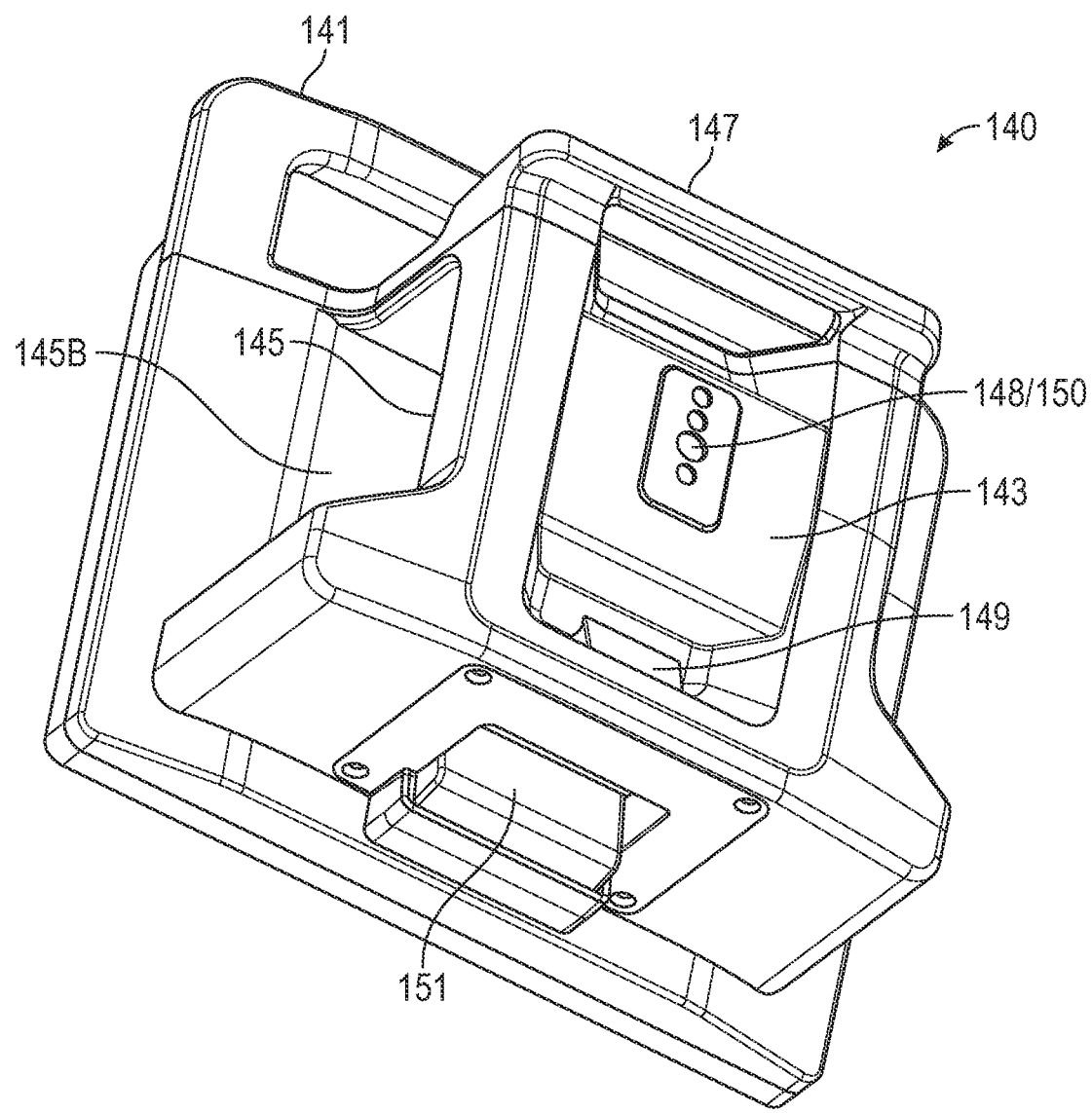
FIG. 16 is a bottom perspective view of the first exemplary implementation of the second monitor 140.

FIG. 16 is a rear perspective view of the first exemplary implementation of the second monitor 140. As illustrated in FIG. 16, the second monitor 140 has another handle 151 linked to the latch 149. In some variations, the second monitor 140 may be removed from the monitor mount 160 by pressing the handle 151 so as to disengage the latch 149 from the slot 169 defined in the coupling 170 of the monitor mount 160. For example, the handle 151 may be located underneath the latch 149 on an underside of the second monitor 140 and a user may grip the underside of the second monitor 140 so as to operate the handle 151.

Figure 17:
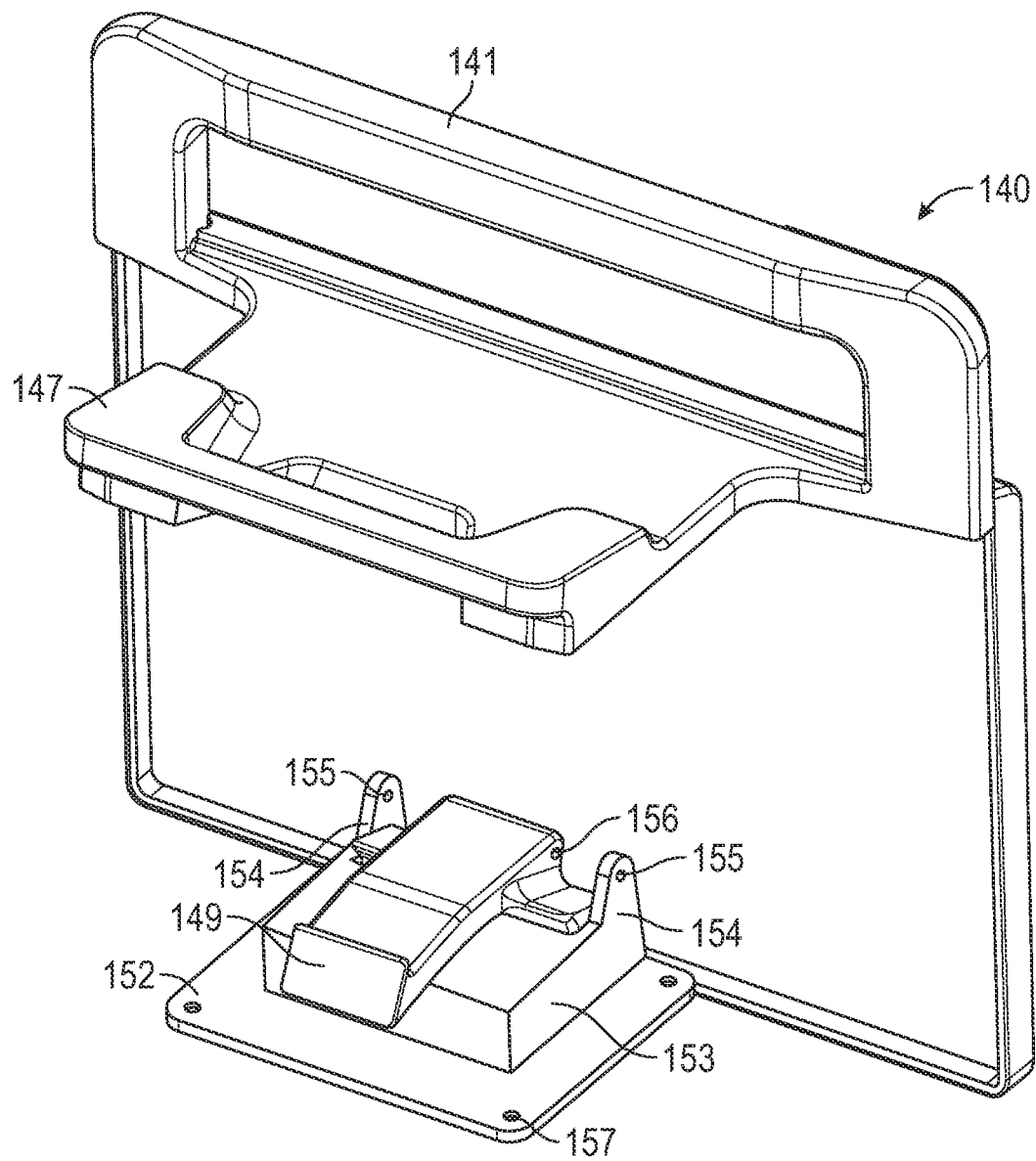
FIG. 17 is a rear perspective view of the first exemplary implementation of the second monitor 140 with a rear housing thereof removed.

FIG. 17 is a rear perspective view of the first exemplary implementation of the second monitor 140 with a rear housing thereof removed. As illustrated in FIG. 17, the second monitor 140 includes a base plate 152 and a latch cover 153 fixed to the base plate 152. In some variations, the latch 149 is configured to pivot relative to the latch cover 153. The latch cover 153 may include at least one protrusion 154 extending away from the base plate 152, and an aperture 155 defined in the at least one protrusion 154. An aperture 156 may also be defined in the latch 149. In some variations, the aperture 155 may be defined adjacent to a distal end of the at least one protrusion 154 and the aperture 156 may be defined adjacent to a proximal end of the latch 149. Each of the apertures 155, 156 may be configured to receive an axle rod (not shown) around which the latch 149 is pivotable and which extends through the latch 149 and the latch cover 153. For example, the axle rod may be cylindrical and may extend along a longitudinal direction of the second monitor 140. As described above, the latch 149 may be spring-loaded such that the latch 149 is biased into the slot 169 (shown in FIG. 6) when the second monitor 140 is being detachably secured to the monitor mount 160. For example, the second monitor 140 may include at least one spring (not shown) between the latch 149 and the latch cover 153 for biasing the latch 149 into the slot 169. The second monitor 140 may further include any mounting interface 157 such as a VESA mounting interface.

Figure 18:
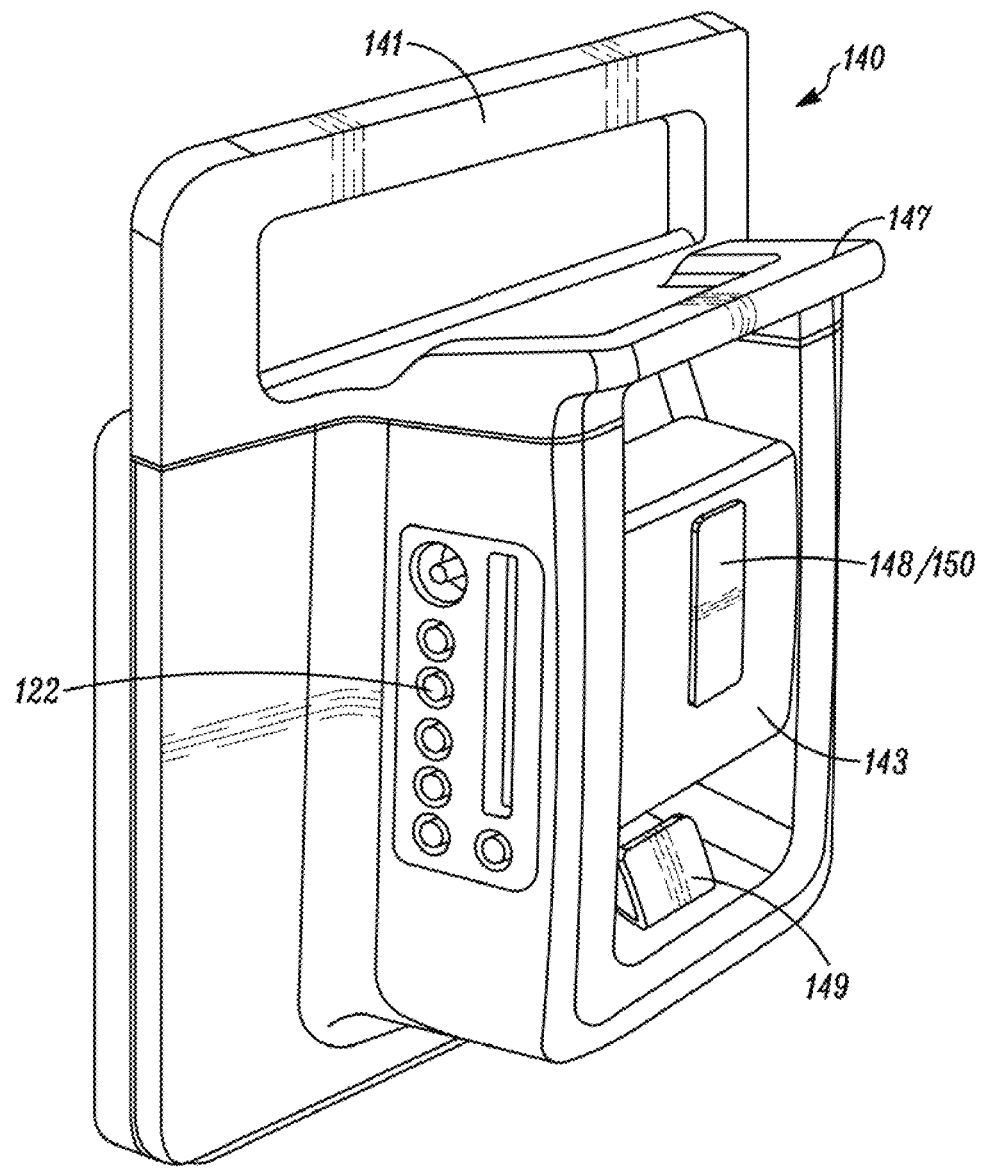
FIG. 18 is a rear perspective view of a second exemplary implementation of the second monitor 140.

FIG. 18 is a rear perspective view of a second exemplary implementation of the second monitor 140. For example, a smaller monitor (e.g., first monitor 120) is used to monitor various physiological parameters for a patient 110, and a larger monitor (e.g., second monitor 140) is used to expand the number of sensors available for patient monitoring and/or increasing the number of patient parameters on a single visual electronic display. In other words, the smaller monitor can generally include a sensor interface configured to receive data generated by at least one physiological sensor monitoring a physiological parameter of a patient. The larger monitor can be a multiparameter monitor for continuously monitoring adult, pediatric and neonatal patients both at a bedside and on transport and can support all patient acuity levels hospital-wide.

In some variations, only one of the first monitor 120 and the larger monitor 140 is provided. In some variations, both of the first monitor 120 and the second monitor 140 are provided and the first monitor 120 is docked in the second monitor 140. As illustrated in FIG. 18, the second monitor 140 integrates the functionalities of a smaller monitor and a larger monitor into one single unit and includes the sensor interface 122. In the embodiment shown in FIG. 18, the second monitor 140 further includes a handle 141, a hook portion 147, a communications interface 148, a latch 149, and a power source and/or conduit 150. In the embodiment shown in FIG. 18, the second monitor 140 does not include a second coupling 145. The back portion 143 of the monitor 140 shown in FIG. 18 can be reduced in thickness compared to the back portion 143 of the monitor 140 shown in FIG. 15 and therefore has a slimmer overall volume.

Figure 19:
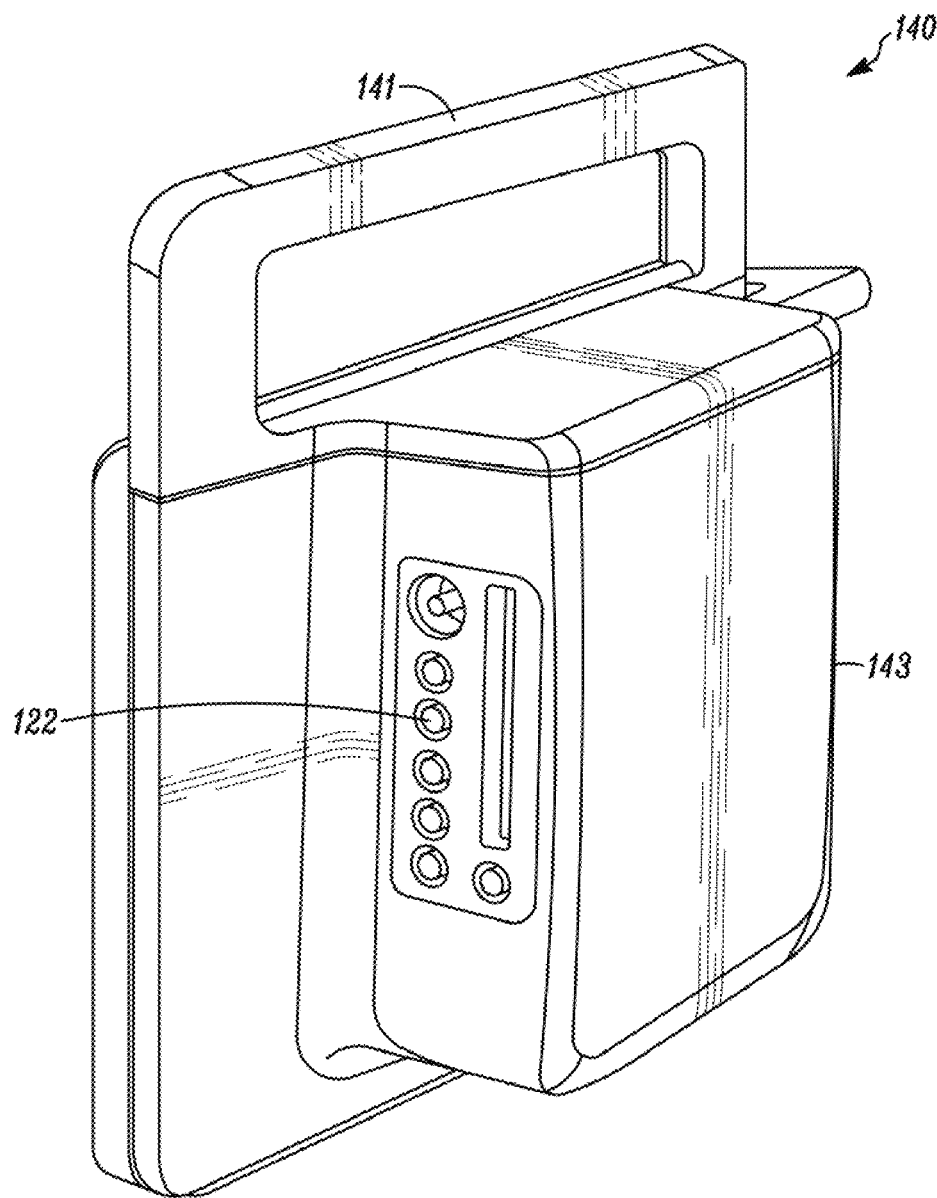
FIG. 19 is a rear perspective view of a third exemplary implementation of the second monitor 140.

FIG. 19 is a rear perspective view of a third exemplary implementation of the second monitor 140. As illustrated in FIG. 19, the second monitor 140 integrates the functionalities of a smaller monitor and a larger monitor into one single unit and includes the sensor interface 122. In the embodiment shown in FIG. 19, the second monitor 140 has a handle 141 and a simplified back portion 143. That is, a back surface of the back portion 143 is continuous and the back surface does not include couplings or electrical connections. In other words, in the embodiment shown in FIG. 19, the second monitor does not include a second coupling 145, a hook portion 147, a communications interface 148, a latch 149, or a power source and/or conduit 150. The back portion 143 of the monitor 140 shown in FIG. 19 can be reduced in thickness compared to the back portion 143 of the monitor 140 shown in FIG. 15 and therefore has a slimmer overall volume.

FIGS. 20-24 show various exemplary implementations of a system including a rack 200 for detachably securing a module 300. The rack 200 can detachably secure the module 300 in a first position in which a first electrical connector 201 of the rack 200 and a second electrical connector 301 of the module 300 are electrically connected and the module 300 and the rack 200 are mechanically connected. The rack 200 can also detachably secure the module 300 therein in a second position in which the first electrical connector 201 and the second electrical connector 301 are electrically disconnected and the module 300 and the rack 200 are mechanically connected. In other words, the module 300 remains mechanically connected to the rack 200 in both the first position and the second position; i.e., the module 300 can be partially released from the rack 200 and electrically disconnected while still being mechanically retained. In this way, the rack 200 can catch and hold the module 300 in a secondary position such that the module 300 is docked, but power to the module 300 is cut while other connections such as gas and/or pump connections (e.g., electroencephalogram (EEG), Neuro Muscular Transmission (NMT), gas analysis, electrocardiogram (EKG or ECG), SPO2, blood pressure, etc.) are maintained. In the embodiments shown in FIGS. 20 & 21, sides of the rack 200 are closed. In other embodiments not shown, sides of the rack 200 may be open. The module 300 may further include one or more third electrical connectors 304 such as a circular connector for electrical connection with another device outside the rack 200.

In the embodiments shown in FIGS. 20-24, the module 300 includes a latch 303 adapted to engage with first and second recesses 202, 203 in the rack 200. The first and second recesses 202, 203 can be located on an upper surface of a lower portion the rack 200 at different positions along a depth direction of the rack 200. In the first position, the latch 303 may be engaged in the first recess 202. In the second position, the latch 303 may be engaged in the second recess 203. The release of the module 300 can be affected by a releaser 302 (as shown in FIG. 22A) which may be a tab configured to release the latch 303 from engagement and allow removal of the module 300 from the rack 200.

Figure 22B:
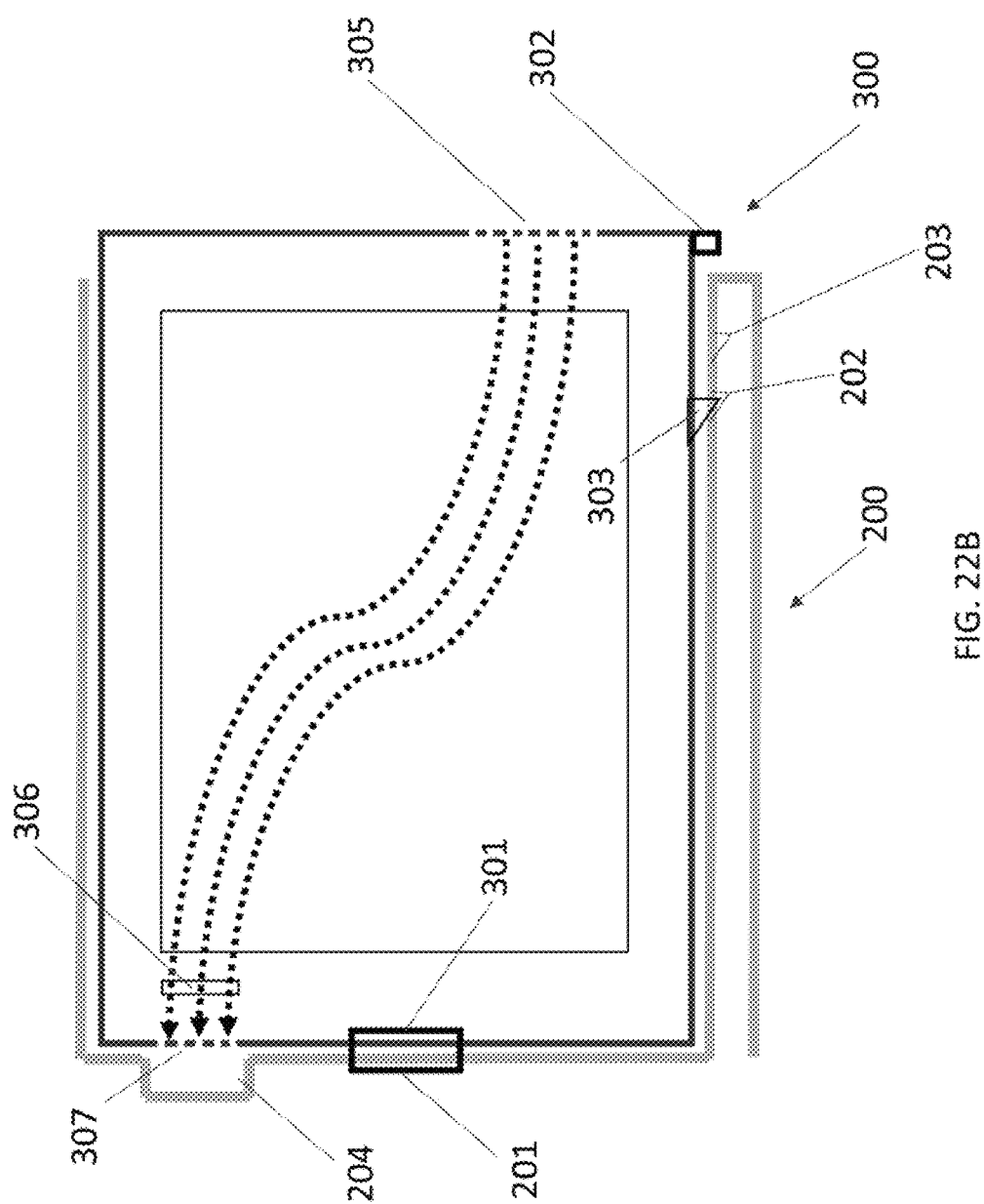
FIG. 22B is a cross-sectional view of the exemplary implementation of the rack 200 detachably securing the exemplary implementation of the module 300.
Figure 23:
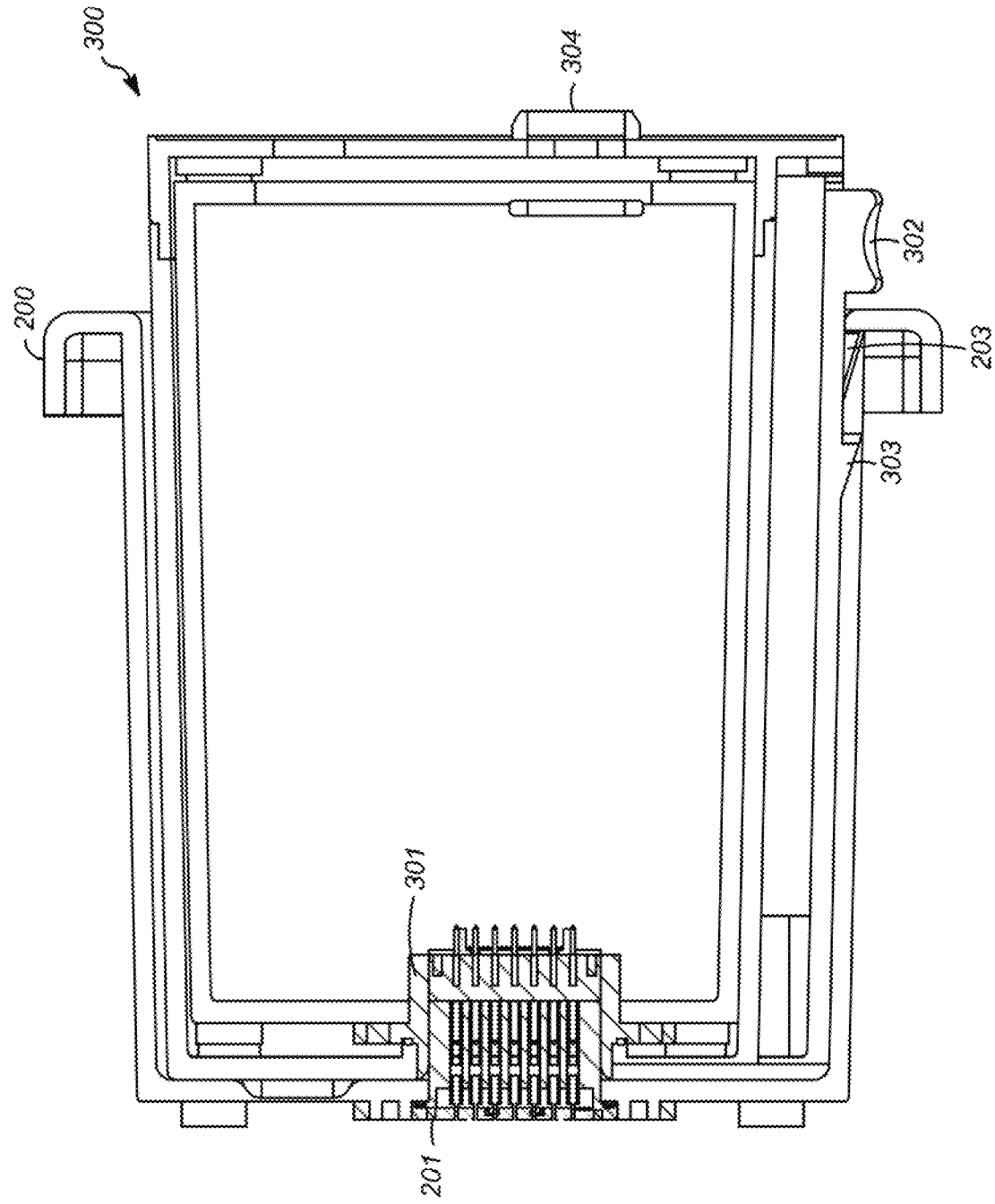
FIG. 23 is another cross-sectional view of the exemplary implementation of the rack 200 detachably securing the exemplary implementation of the module 300.
Figure 24:
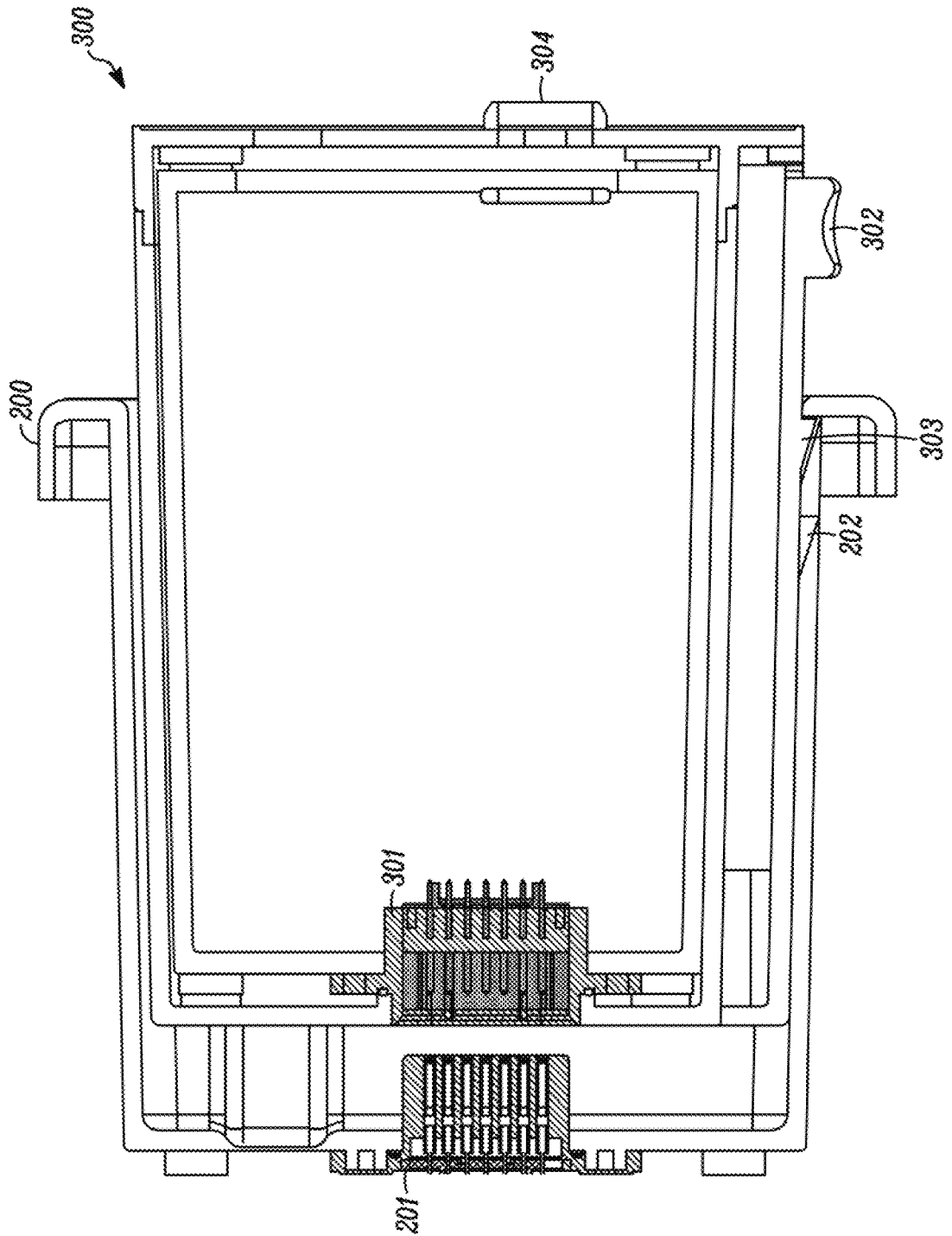
FIG. 24 is a further cross-sectional view of the exemplary implementation of the rack 200 detachably securing the exemplary implementation of the module 300.

A channel 204 may be defined in a back wall of the rack 200. The channel 204 may provide a space between the back wall of the rack 200 and the module 300 when the module 300 is detachably secured in the rack 200. The channel 204 can vent air from the back of any module 300 requiring cooling and exhaust the air out of the front of the rack 200 thereby assisting with thermal mitigation. The channel 204 may extend across one or more sides of the rack 200. For example, the channel 204 may extend across three sides of the rack 200. As shown in FIG. 22B, the module 300 may further comprise an air inlet 305 and an air outlet 307 configured to vent air to the channel 204 of the rack 200. Such venting further assists with thermal mitigation by drawing heat away from internal elements of the module 300 (e.g., a circuit board of the module 300). In addition, the module 300 may further comprise at least one fan 306 for circulating air to the air outlet 307. Accordingly, active airflow can be provided by the module 300 to the rack 200.

The rack 200 may include one or more guide rails 205 each defining one side of a bay for receiving the module 300. The rack can include any number of guide rails 205, for example, in the illustrated embodiment, three guide rails 205 may be provided such that the rack 200 has four bays. A length of each of the guide rails 205 may be less than a depth of the rack 200. Such a partial guide rail length improves cleanability (e.g., the ease with which the device may be clean and/or sanitized between patients and uses) of the rack 200 because there is a continuous flat section close to an opening of the rack 200 and there are fewer surfaces to be cleaned.

The rack 200 may include an electrical connector 201 which protrudes through an aperture defined in the back wall of the rack 200 for connection to an electrical connector 301 of the module 300. The electrical connector 301 may be recessed in the module 300. The rack 200 may also include any mounting interface such as a VESA mounting interface. Therefore, the rack 200 enables a user to store modules 300 in an additional position in which the modules 300 are physically or mechanically connected to the rack 200 but electrically disconnected from the rack 200.

FIG. 25 is a front perspective view of a cable holder 400. As shown in FIG. 25, the cable holder 400 may comprise a back wall 401 and a side wall 402. The side wall 402 may extend from one end of the back wall 401. The side wall 402 may include apertures 403-405 defined therein. Each of the apertures 403-405 may be configured to receive a cable 600 therethrough. A first of the apertures 403 may be arcuate. A second of the apertures 404 may be parallelogram-shaped and oblique with respect to the back wall 401. A third of the apertures 405 may be rectangular and perpendicular to the back wall 401. The side wall 402 may further include a notch 406 at one end thereof. In addition, the third of the apertures 405 may have a first end at a distal end of the side wall 402 and a second end adjacent to a proximal end of the side wall 402 and a width of the first end of the third of the apertures 405 may be less than a width of the second end of the third of the apertures 405. In addition, the side wall 402 may be one of two side walls 402 at respective ends of the back wall 401.

FIG. 26 is a front perspective view of the cable holder 400 detachably securing a cable 600. As shown in FIG. 26, the cable 600 may include a housing portion 601. The housing portion 601 may, for example, be configured to house a translator configured to translate protocols across cable portions 602 on respective sides of the housing portion 601. As shown in FIG. 26, the cable holder 400 may be configured to detachably secure the cable 600 such that the housing portion 601 of the cable 600 rests on a side wall 402 of the cable holder 400.

FIG. 27 is a front perspective view of a cable holder 500. FIG. 28 is a bottom perspective view of the cable holder 500. As shown in FIGS. 27 & 28, the cable holder 500 may comprise a back wall 501, a side wall 502, a front wall 503, and projections 506. The side wall 502 may extend from a first end of the back wall 501. The side wall 502 may include apertures 504 defined therein. The front wall 503 may extend from an end of the side wall 502 opposite to the back wall 501. The front wall 503 may include slots 505 defined therein. The projections 506 may extend from a second end of the back wall 501. Each of the apertures 504 and the slots 505 may be configured to receive a cable 600 therethrough such that the cable 600 is positioned between two of the projections 506. As shown in FIG. 28, the apertures 504 may be polygonal. Each of the slots 505 may have a first end at a distal end of the front wall 503 and a second end at a proximal end of the front wall 503. For each of the slots 505, a width of the first end of the slot 505 may be greater than a width of the second end of the slot 505.

FIG. 29 is a front perspective view of the cable holder 500 detachably securing a cable 600. As shown in FIG. 29, the cable 600 may include a housing portion 601. The housing portion 601 may, for example, be configured to house a translator configured to translate protocols across cable portions 602 on respective sides of the housing portion 601. As shown in FIG. 29, the cable holder 500 may be configured to detachably secure the cable 600 such that the housing portion 601 of the cable 600 rests on a side wall 502 of the cable holder 500. In addition, as shown in FIG. 29, the cable holder 500 may be configured to detachably secure the cable 600 such that the housing portion 601 of the cable 600 is positioned between two of the projections 506 of the cable holder 500.

Although various embodiments have been described above, these are to be regarded as merely examples. Accordingly, those of ordinary skill in the art will recognize that various changes and modifications of the examples described herein can be made without departing from the spirit and scope of the present disclosure. For example, any feature of any particular portion, embodiment or modification of the monitors 120, 140 may be included or omitted from any of the other portions, embodiments or modifications of the monitors 120, 140. Any feature of any particular portion, embodiment or modification of the monitor mount 160 may be included or omitted from any of the other portions, embodiments or modifications of the monitor mount 160. Any feature of any particular portion, embodiment or modification of the rack 200 may be included or omitted from any of the other portions, embodiments or modifications of the rack 200. Any feature of any particular portion, embodiment or modification of the module 300 may be included or omitted from any of the other portions, embodiments or modifications of the module 300. Any feature of any particular portion, embodiment or modification of the cable holders 400, 500 may be included or omitted from any of the other portions, embodiments or modifications of the cable holders 400, 500. Any feature of any particular portion, embodiment or modification of the cable 600 may be included or omitted from any of the other portions, embodiments or modifications of the cable 600. Any feature of any particular portion, embodiment or modification of any device of the system and any support structure can be detachably secured to or otherwise physically interface with each other via any mounting interface such as a VESA mounting interface. Furthermore, any embodiment or modification of the rack 200 can detachably secure (or otherwise physically interface with) any embodiment or modification of the module 300. In addition, any embodiment or modification of the cable holders 400, 500 can detachably secure any embodiment or modification of the cable 600.

Further, it is noted that the present disclosure may be implemented as any combination of a system, an integrated circuit, and a computer program on a non-transitory computer readable recording medium. The processor and any other parts of the computing system may be implemented as Integrated Circuits (IC), Application-Specific Integrated Circuits (ASIC), or Large Scale Integrated circuits (LSI), system LSI, super LSI, or ultra LSI components which perform a part or all of the functions of the computing system.

Each of the parts of the present disclosure can be implemented using many single-function components, or can be one component integrated using the technologies described above. The circuits may also be implemented as a specifically programmed general purpose processor, CPU, a specialized microprocessor such as Digital Signal Processor that can be directed by program instructions on a memory, a Field Programmable Gate Array (FPGA) that can be programmed after manufacturing, or a reconfigurable processor. Some or all of the functions may be implemented by such a processor while some or all of the functions may be implemented by circuitry in any of the forms discussed above.

The present disclosure may be implemented as a non-transitory computer-readable recording medium having recorded thereon a program embodying methods/algorithms for instructing the processor to perform the methods/algorithms. The non-transitory computer-readable recording medium can be, for example, a CD-ROM, DVD, Blu-ray disc, or an electronic memory device.

Each of the elements of the present disclosure may be configured by implementing dedicated hardware or a software program on a memory controlling a processor to perform the functions of any of the components or combinations thereof. Any of the components may be implemented as a CPU or other processor reading and executing a software program from a recording medium such as a hard disk or a semiconductor memory.

It is also contemplated that the implementation of the components of the present disclosure can be done with any newly arising technology that may replace any of the above implementation technologies.

The system of the present disclosure is a modular system providing a universal and scalable platform including a monitor mount capable of mixed use with monitors having different sizes. Traditionally, each type of patient monitor typically required a dedicated monitor mount, a dedicated controller, and a dedicated user interface. Accordingly, traditional monitors of different sizes are not interoperable and the performance advantages of each type of monitor cannot be combined and leveraged. However, since the system of the present disclosure enables the mounting of two monitors having different sizes, shapes, and functionality on a single monitor mount, the two monitors are interoperable with the same controller and the same user interface, and can be universally docked to the monitor mount.

The monitor mount of the present disclosure can be both quickly and rigidly secured to mobile or transportable support structures in addition to stationary support structures. The monitor mount of the present disclosure, therefore, addresses deficiencies of difficulty in both quickly and rigidly securing devices to mobile or transportable support structures such as bed or stretcher or gurney rails, IV poles, ambulance bars, etc. in addition to stationary support structures, and failing to enable a monitor to be attached directly to a tubular or rectangular support structure.

The first monitor of the present disclosure may have a cover that is modular such that it can be reversibly secured in multiple different orientations. The first monitor, therefore, allows for left-hand and right-hand configurations with the same monitor.

The second monitor of the present disclosure may have a simplified back portion. Accordingly, the simplified back portion may have a reduced thickness and the second monitor may have a slimmer overall volume.

The rack of the present disclosure can store modules in an additional position in which the modules are physically connected to the rack but electrically disconnected from the rack. The rack of the present disclosure, therefore, addresses deficiencies of only being able to secure modules in one position inside a rack, and electrically disconnected modules falling or dropping out of the rack due to gravity.

The cable holders of the present disclosure can provide flexibility in manufacturing, mounting and cable management. Cables can be easily secured by the cable holders rather than dangling and causing inconvenience on transport or at a stationary setting. Such a cable management solution frees up space and is helpful with respect to seamless workflow in a variety of areas such as monitoring, anesthesia, and information technology workstations. The system of the present disclosure provides a universal and scalable platform including cable holders capable of being quickly secured to and released from a support structure and preventing fraying or tangling of one or more cables configured to physically and electrically connect to one or more devices such as patient monitoring devices.

What is claimed is:
1. A system, comprising:
a rack having a back wall and a lower portion, the lower portion having an upper surface and defining a first recess and a second recess in the upper surface thereof;

a first electrical connector on the back wall of the rack; and
a medical monitor module including:
a latch for selectively engaging the first recess and the second recess to mechanically retain the module in a respective first position and a respective second position in the rack; and
a second electrical connector on a back surface thereof, the second electrical connector being:
electrically connected to the first electrical connector when the medical monitor module is mechanically retained in the rack in the first position; and
electrically disconnected from the first electrical connector when the medical monitor module is mechanically retained in the second position.

2. The system of claim 1, further comprising:
a releaser on the medical monitor module for transitioning the medical monitor module between the first and second recesses and to allow removal of the medical monitor module from the rack.

3. The system of claim 1, further comprising:
a third electrical connector on a front surface of the medical monitor module.

4. The system of claim 1, further comprising:
an air inlet on a front surface of the monitor, and an air outlet on the back surface of the medical monitor module; and
a fan in the medical monitor module for circulating air from the air inlet to the air outlet.

5. The monitor system of claim 4, further comprising:
a channel on the back wall defining a space between the back wall of the rack and the medical monitor module to vent air from the air outlet of the medical monitor module toward the front surface of the medical monitor module when the medical monitor module is mechanically retained in the rack.

6. A method of detachably securing a medical monitor module to a rack, comprising:
providing a first electrical connector on the back wall of the rack;
providing a first recess in an upper surface of a lower portion of the rack, and a second recess in the upper surface of the lower portion of the rack;
providing a latch on the medical monitor module for selectively engaging the first recess and the second recess to mechanically retain the module in respective first and second positions in the rack;
providing a second electrical connector on a back surface of the monitor, the second electrical connector being:
electrically connected to the first electrical connector when the medical monitor module is mechanically retained in the rack in the first position; and
electrically disconnected from the first electrical connector when the medical monitor module is mechanically retained in the second position.

7. The method of claim 6, further comprising:
providing a releaser on the medical monitor module for disengaging the latch from the first and second recesses to allow removal of the medical monitor module from the rack.

8. The method of claim 6, further comprising:
providing a third electrical on a front surface of the medical monitor module.

9. The method of claim 6, further comprising:
providing an air inlet on a front surface of the medical monitor module,
providing an air outlet on the back surface of the medical monitor module; and
providing a fan in the medical monitor module for circulating air from the air inlet to the air outlet.

10. The method of claim 9, further comprising:
providing a channel on the back wall defining a space between the back wall of the rack to and the medical monitor module to vent air from the air outlet of the medical monitor module toward the front surface of the medical monitor module when the medical monitor module is mechanically retained in the rack.

11. A monitor system, comprising:
a rack having a back wall and a lower portion;
a plurality of guide rails on the lower portion of the rack defining a plurality of module bays of the rack, each bay including:
a first electrical connector on the back wall of the rack;
a first recess in an upper surface of the lower portion, and a second recess in the upper surface of the lower portion;
at least one medical monitor module having a second electrical connector on a back surface thereof and having a latch for selectively engaging the first recess and the second recess of a selected one of the plurality of bays to mechanically retain the module in respective first and second positions in the selected bay, the second electrical connector being:
electrically connected to the first electrical connector of the selected bay when the medical monitor module is mechanically retained in the first position in the selected bay; and
electrically disconnected from the first electrical connector of the selected bay when the medical monitor module is mechanically retained in the second position in the selected bay.

12. The monitor system of claim 11, further comprising:
a releaser on the at least one medical monitor module for disengaging the latch from the first and second recesses to allow removal of the medical monitor module from the selected bay.

13. The monitor system of claim 11, further comprising:
a third electrical connector on a front surface of the at least one medical monitor module.

14. The monitor system of claim 11, further comprising:
an air inlet on a front surface of the at least one medical monitor module,
an air outlet on the back surface of the at least one medical monitor module; and
a fan in the at least one medical monitor module for circulating air from the air inlet to the air outlet.

15. The monitor system of claim 14, further comprising:
a channel on the back wall defining a space between the back wall of the rack and the at least one medical monitor module to vent air from the air outlet of the medical monitor module toward the front surface of the medical monitor module when the at least one medical monitor module is mechanically retained in the selected bay.

* * * * *